United States Patent [19]

Koths et al.

[11] Patent Number: 5,116,943
[45] Date of Patent: May 26, 1992

[54] OXIDATION-RESISTANT MUTEINS OF IL-2 AND OTHER PROTEIN

[75] Inventors: Kirston E. Koths, El Cerrito; Robert F. Halenbeck, San Rafael; both of Calif.; David F. Mark, Plainsboro, N.J.; Danutee Nitecti, Berkeley, Calif.

[73] Assignee: Cetus Corporation, Emeryville, Calif.

[21] Appl. No.: 192,293

[22] Filed: May 10, 1988

Related U.S. Application Data

[60] Division of Ser. No. 893,186, Aug. 5, 1986, Pat. No. 4,752,585, which is a continuation-in-part of Ser. No. 810,656, Dec. 17, 1985, abandoned, which is a continuation-in-part of Ser. No. 692,596, Jan. 18, 1985, abandoned.

[51] Int. Cl.$^5$ ................. C07K 13/00; A61K 37/00
[52] U.S. Cl. .................... 530/351; 530/820; 530/825; 435/69.52; 435/69.51; 435/69.5; 424/85.2; 424/85.1; 424/85.4; 424/85.5; 424/85.6; 424/85.7
[58] Field of Search ............ 530/351, 820, 825; 435/69.52, 69.51, 69.5; 424/85.2, 85.1, 85.4, 85.5, 85.6, 85.7

[56] References Cited

U.S. PATENT DOCUMENTS

| 4,738,927 | 4/1988 | Taniguchi et al. | 435/69.52 |
| 4,760,025 | 7/1988 | Estell et al. | 435/222 |
| 4,761,375 | 8/1988 | Clark | 435/320 |

FOREIGN PATENT DOCUMENTS 8700817 2/1985 PCT Int'l Appl. .

OTHER PUBLICATIONS

Zoaller et al., *NA*, 10, 1982, pp. 64787–6500.
Wells et al., *Gene* 34, 1985, pp. 315–323.
Bauer et al., *Gene* 37, 1985, pp. 73–81.
Lee et al., *Bochem Biophys Res. Comm* 1988, pp. 807–813, vol. 156(2).
Leatherbarrow et al., *Protein Engineering*, vol. 1, 1986, pp. 7–16.

*Primary Examiner*—Garnette D. Draper
*Attorney, Agent, or Firm*—Philip L. McGarrigle; Lisabeth F. Murphy

[57] ABSTRACT

A biologically active reference therapeutic protein is protected against oxidation by a method involving substituting a conservative amino acid for each methionyl residue susceptible to chloramine T or peroxide oxidation, wherein additional, non-susceptible methionyl residues are not so substituted. The oxidation-resistant mutein so produced is preferably a human mutein of interleukin-2 or interferon-β, and the conservative amino acid is most preferably alanine.

13 Claims, 5 Drawing Sheets

|  | 5 | 10 | 15 | 20 |
|---|---|---|---|---|
| AlaProThrSerSer | SerThrLysLysThr | GlnLeuGlnLeuGlu | HisLeuLeuLeuAsp |
|  | 25 | 30 | 35 | 40 |
| LeuGlnMetIleLeu | AsnGlyIleAsnAsn | TyrLysAsnProLys | LeuThrArgMetLeu |
|  | 45 | 50 | 55 | 60 |
| ThrPheLysPheTyr | MetProLysLysAla | ThrGluLeuLysHis | LeuGlnCysLeuGlu |
|  | 65 | 70 | 75 | 80 |
| GluGluLeuLysPro | LeuGluGluValLeu | AsnLeuAlaGlnSer | LysAsnPheHisLeu |
|  | 85 | 90 | 95 | 100 |
| ArgProArgAspLeu | IleSerAsnIleAsn | ValIleValLeuGlu | LeuLysGlySerGlu |
|  | 105 | 110 | 115 | 120 |
| ThrThrPheMetCys | GluTyrAlaAspGlu | ThrAlaThrIleVal | GluPheLeuAsnArg |
|  | 125 | 130 | 135 | 140 |
| TrpIleThrPheCys | GlnSerIleIleSer | ThrLeuThr--- |  |

FIG._1

|  | 5 | 10 | 15 | 20 |
|---|---|---|---|---|
| MetSerTyrAsnLeu | LeuGlyPheLeuGln | ArgSerSerAsnPhe | GlnCysGlnLysLeu |
|  | 25 | 30 | 35 | 40 |
| LeuTrpGlnLeuAsn | GlyArgLeuGluTyr | CysLeuLysAspArg | MetAsnPheAspIle |
|  | 45 | 50 | 55 | 60 |
| ProGluGluIleLys | GlnLeuGlnGlnPhe | GlnLysGluAspAla | AlaLeuThrIleTyr |
|  | 65 | 70 | 75 | 80 |
| GluMetLeuGlnAsn | IlePheAlaIlePhe | ArgGlnAspSerSer | SerThrGlyTrpAsn |
|  | 85 | 90 | 95 | 100 |
| GluThrIleValGlu | AsnLeuLeuAlaAsn | ValTyrHisGlnIle | AsnHisLeuLysThr |
|  | 105 | 110 | 115 | 120 |
| ValLeuGluGluLys | LeuGluLysGluAsp | PheThrArgGlyLys | LeuMetSerSerLeu |
|  | 125 | 130 | 135 | 140 |
| HisLeuLysArgTyr | TyrGlyArgIleLeu | HisTyrLeuLysAla | LysGluTyrSerHis |
|  | 145 | 150 | 155 | 160 |
| CysAlaTrpThrIle | ValArgValGluIle | LeuArgAsnPheTyr | PheIleAsnArgLeu |
|  | 165 | 170 | 175 | 180 |
| ThrGlyTyrLeuArg | Asn--- |  |  |

FIG._2

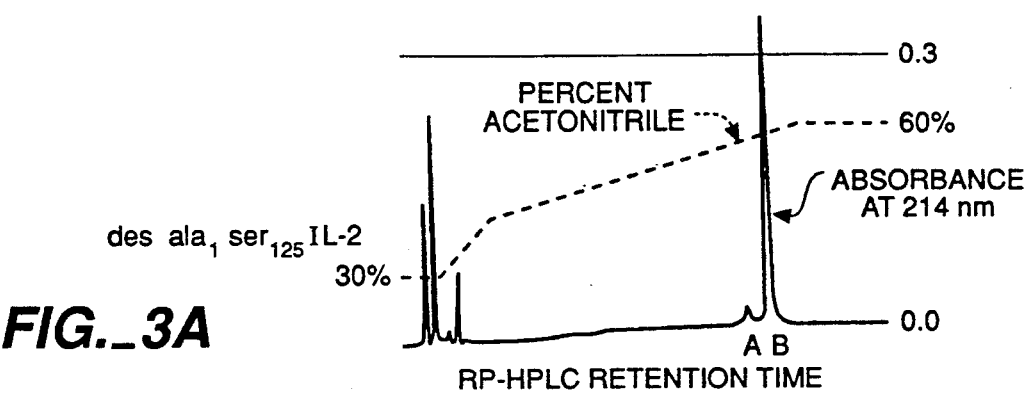
FIG._3A
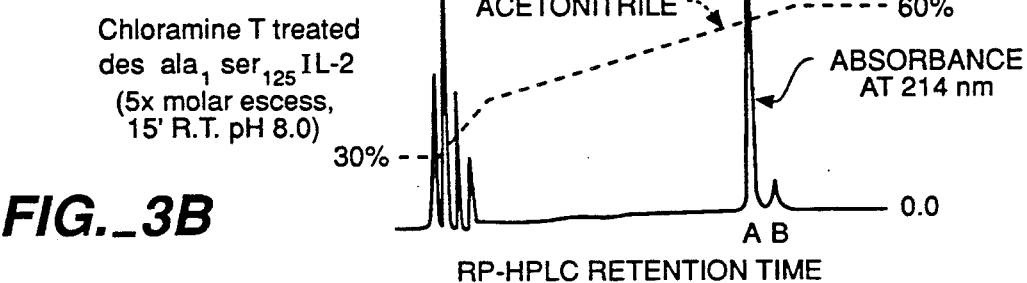
FIG._3B
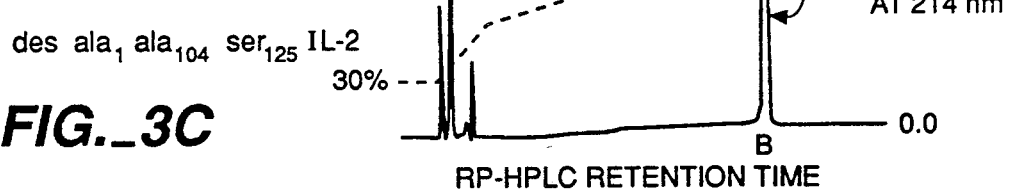
FIG._3C
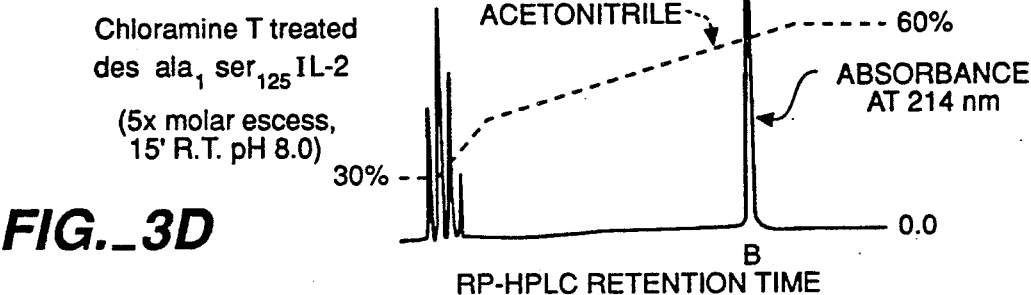
FIG._3D

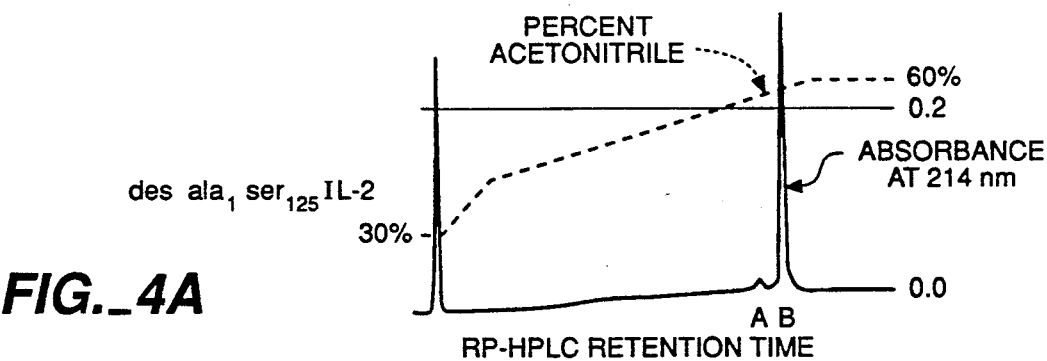
FIG._4A
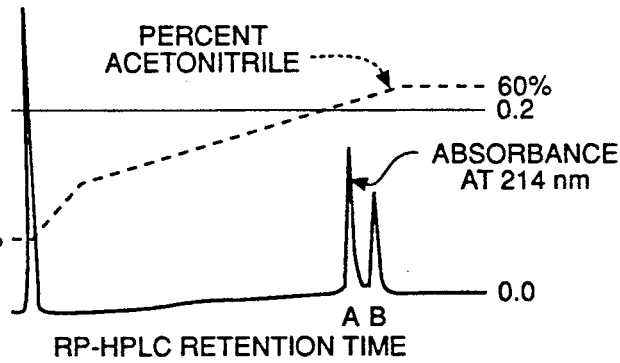
FIG._4B
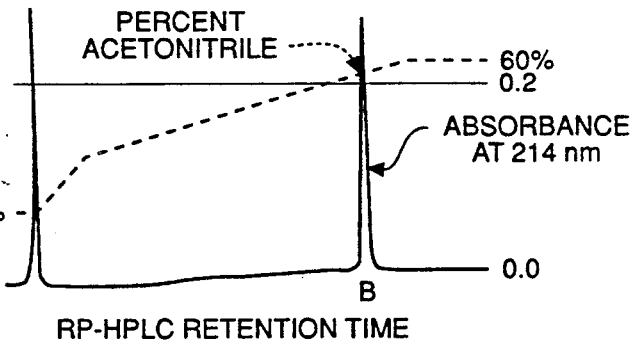
FIG._4C
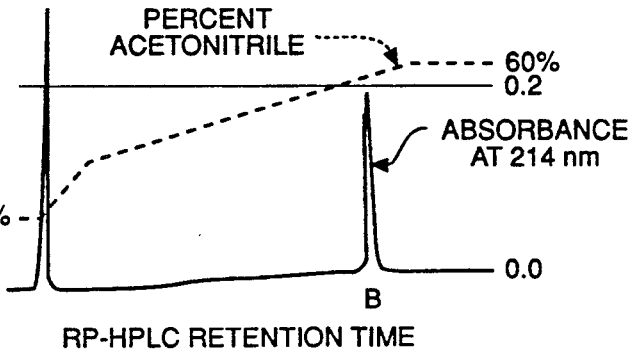
FIG._4D

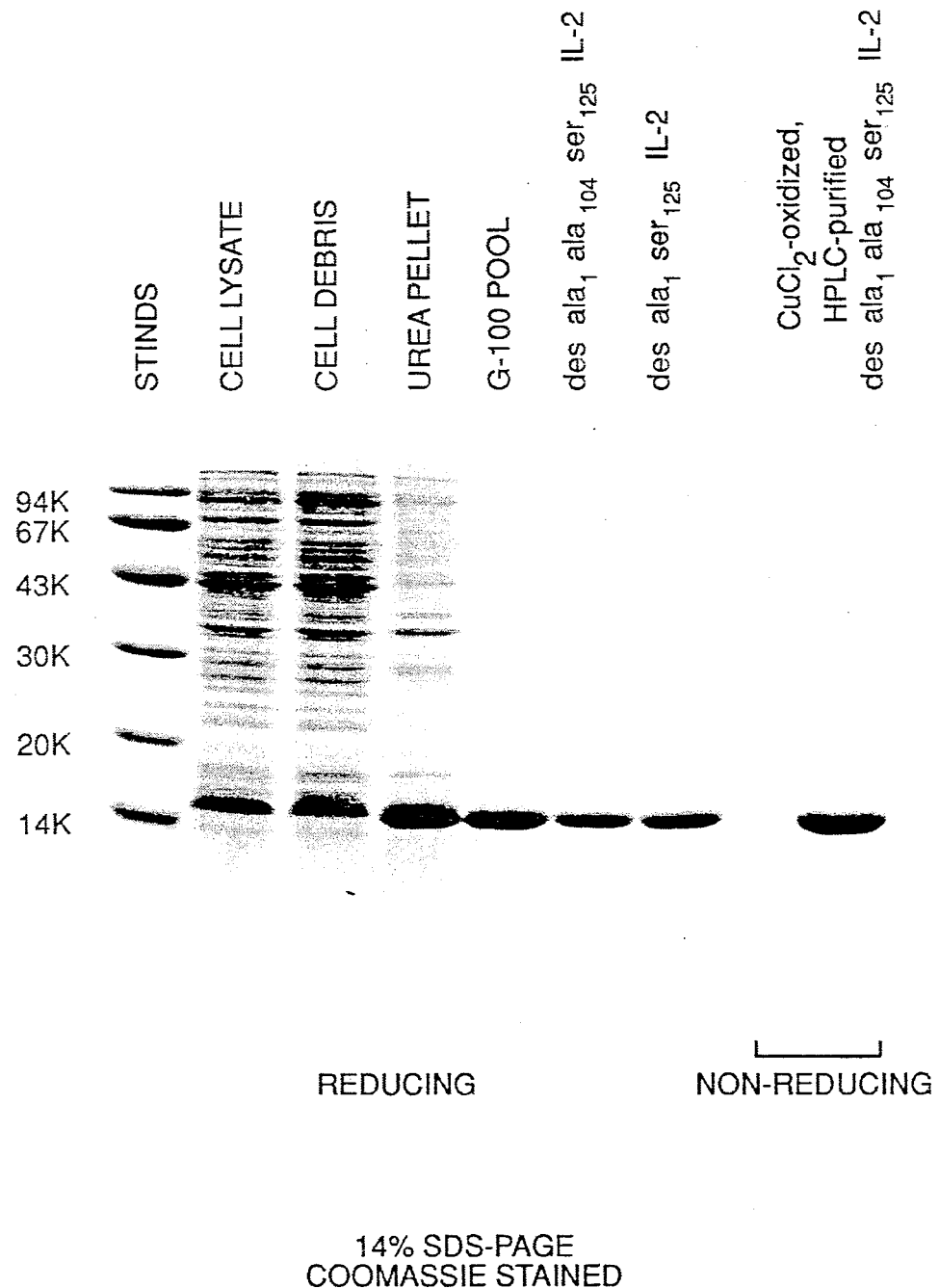
FIG._5

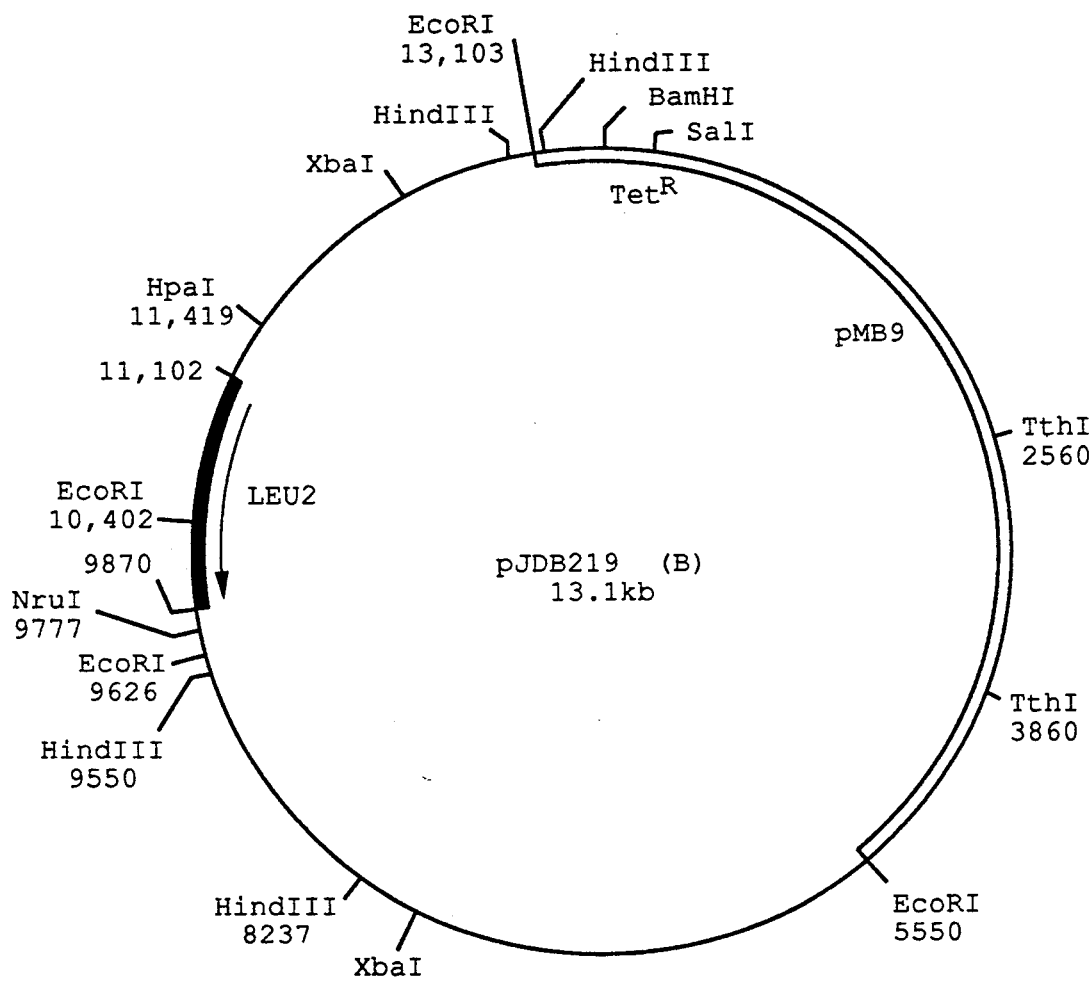
FIG._6

OXIDATION-RESISTANT MUTEINS OF IL-2 AND OTHER PROTEIN

This is a division of Ser. No. 893,186, filed Aug. 5, 1986, now U.S. Pat. No. 4,752,585 which is a continuation-in-part application of copending U.S. application Ser. No. 810,656 filed Dec. 17, 1985 now abandoned which is a continuation-in-part application of copending U.S. application Ser. No. 692,596 filed Jan. 18, 1985 now abandoned.

BACKGROUND OF THE INVENTION

1. Technical Field

The invention relates to the use of recombinant techniques to provide modified protein sequences resistant to oxidation, i.e., oxidation-receptive proteins. More specifically, the invention relates to providing proteins which retain useful biological activity, but which contain conservative amino acid substitutions for specific methionine residues that are particularly susceptible to oxidation.

2. Background Art

The fact that different proteins undergo varying degrees of modification during purification is well known, but not well understood. Certain proteins are known to be unusually susceptible to thermal denaturation or to proteolytic cleavage; other contain reactive amino acid side chains located in positions which render them particularly susceptible to chemical modification, including oxidation. In general, it is not possible to predict from the amino acid sequence the extent to which any of the above modifications will occur.

This problem is compounded because ordinary preparative methods for protein purification may lack the resolution to detect or separate small amounts of impurities. Such commonly employed techniques and criteria for homogeneity as electrophoresis, gel filtration, and ion exchange chromatography may fail to reveal the presence of small amounts of contaminating material which can be shown to be present by more sensitive analytical techniques, such as reverse phase high performance liquid chromatography (RP-HPLC).

Floor, E., et al., *Anal. Biochem.* (1980) 101:498–503 describes an illustration of this problem. An undecaprotein which has neurotransmitter properties, substance P, containing a carboxy terminal methionine that is oxidizable to methionine sulfoxide in dilute solutions exposed to air, elutes from ion exchange columns as a single peak, but reveals the presence of the sulfoxide-containing contaminant when subjected to RP-HPLC. Similarly, Frelinger, A. L., et al., *J. Biol. Chem.* (1984) 259:5507–5513 showed that bovine parathyroid hormone which appeared homogeneous by conventional criteria could be shown by RP-HPLC analysis to contain sequences with either one or both of the methionine residues oxidized to the sulfoxide. The proteins were eluted from RP-HPLC in an order directly proportional to the number of methionine residues oxidized.

Recently, Rosenberg, S., et al., *Nature* (1984) 312:77–80 produced a mutagenized human alpha-1 antitrypsin in yeast which contained a valine residue in place of the methionine at the active site, and which retained significant biological activity. This substitution was made to prevent the observed decrease in inhibitory activity toward elastase, caused by oxidation of this methionine, which destroys the protective function of alpha-1 anti-trypsin in the lungs. The valine substitution resulted in an active anti-trypsin which was, unlike the native form, resistant to oxidation by chemical oxidants which may be similar to those released by leukocytes or present in cigarette smoke. Hence, by making this substitution, it is believed that the levels of anti-trypsin needed to be administered could be reduced. Carrell, R., *Nature* (1984) 312:77–80 discloses uses of α-antitrypsin mutants such as the Rosenberg et al. mutant in which methionine is replaced by valine. Transgene S.A. has replaced the methionine of α-antitrypsin with arginine, presented on May 20, 1985.

When a methionine is located at or near an active site, as in alpha-1 anti-trypsin, and is clearly crucial to biological activity, its oxidation to the sulfoxide might be expected to be detrimental. However, the effects of oxidation during purification of proteins containing several methionine residues which are not at the active site is less clear. Data for a number of proteins containing oxidized methionine residues show this oxidation to have varying degrees of negative effects on activity. At a minimum, the putatively pure protein obtained will, if the oxidized form is not separated away, contain a contaminant, and will therefore not be homogeneous. The effect of the presence of such contaminant(s) per se in, for example, pharmaceutical protein preparations, may be undesirable. Further, the presence of an oxidized methionine may cause other structural changes in the desired protein, such as decreased solubility, increased proteolytic lability, or the inhibition of formation of a required disulfide bond, which may, in turn, have additional side effects, such as the formation of dimeric and higher aggregated forms. Such impurities may be partly responsible for the often observed immunogenicity of parenterally administered proteins, or for other deleterious physiological reactions.

EP 0,130,756 published Jan. 9, 1985 discloses replacing methionine at position 222 of subtilisin with an amino acid such as alanine to provide resistance to oxidation. Estell, D. et al., *J. Biol. Chem.* (1985) 260:6518–6521 discloses mutant subtilisin enzymes whose methionine residues are susceptible to oxidation.

The present invention provides a method for protecting a therapeutic protein which normally contains methionines from oxidation to the methionine sulfoxide during fermentation, purification, storage, and clinical use, by substituting a conservative amino acid for any methionine particularly susceptible to oxidation. Thus protected, the muteins retain useful biological activity and exhibit enhanced chemical stability. They are not subject to contamination by either modified forms containing the methionine sulfoxide per se, or by side products whose formation is the result thereof.

SUMMARY OF THE INVENTION

The invention provides a means to protect specific methionine residues whose preferential oxidation results in therapeutic protein sequences containing methionine sulfoxide residues. Even in small amounts, these impurities may be potential immunogens, and they detract from the homogeneity of the therapeutic product. Even very small amounts of contaminants may be significant, especially for therapeutics injected at high dosage, such as interferons and lymphokines. By providing a conservative amino acid substitution for the susceptible methionine, the applicants believe that one type of protein heterogeneity may be prevented.

Thus, in one aspect, the invention relates to a method for protecting a biologically active reference therapeutic protein against oxidation comprising making a conservative amino acid substitution for each methionyl residue susceptible to chloramine T or peroxide oxidation, where other methionyl residues in the reference protein which are significantly less susceptible are not so substituted. In some cases, the resulting oxidation-resistant mutein will exhibit substantially the same or enhanced specific activity compared to the reference protein. In other cases, the specific activity may be decreased but still therapeutically useful. In all cases, the resulting muteins, which lack oxidation-susceptible methionyl residues, will improve the homogeneity of the preparation by the criteria of RP-HPLC and other analytical techniques which detect methionine sulfoxide. In other aspects, the invention relates to the muteins so produced, recombinant DNA sequences encoding the muteins, recombinant expression vectors comprising the DNA sequence operably linked to control sequences compatible with a suitable host, host cells transformed with the vector, and therapeutic formulations containing certain of the muteins so produced.

Many proteins which are susceptible candidates for the process of the invention contain several methionyl residues, and accordingly, it is preferred to determine which of the methionyl residues is particularly susceptible to oxidation before carrying out the conservative amino acid substitution. Of the four methionines in interleukin-2, the methionine at position 104 has been shown to be preferentially oxidized during conventional purification or exposure to chemical oxidants. Accordingly, in other aspects, the invention relates to IL-2 muteins which harbor conservative amino acid substitutions in position 104 and to therapeutic formulations containing such muteins. In yet other aspects, the invention relates to IFN-$\beta$ muteins which harbor conservative amino acid substitutions in position 62 and to therapeutic formulations containing such muteins. The invention is also applicable to other therapeutic proteins which normally contain one or more susceptible methionines, such as, e.g., colony stimulator factor-1, $\alpha_a$-interferon, gamma-interferon, human growth hormone, tissue plasminogen activator, and urokinase.

BRIEF DESCRIPTION OF THE DRAWINGS

FIG. 1 shows the amino acid sequence of native IL-2, and the position number designations used herein.

FIG. 2 shows the amino acid sequence of native betainterferon (IFN-$\beta$), and the position number designations used herein.

FIGS. 3A-3D show RP-HPLC analysis of both modified and reference IL-2 produced in E. coli, before and after chloramine T treatment.

FIGS. 4A-4D show RP-HPLC analysis of both modified and reference IL-2 produced in E. coli, before and after hydrogen peroxide treatment.

FIG. 5 shows a Coomassie stained SDS-PAGE analysis of extracts or purified IL-2, both from transformed E. coli which produce either the IL-2 mutein of the invention or the reference IL-2.

FIG. 6 shows the restriction map of pJDB219 which may be used as a yeast expression vector. This map represents the B form of this plasmid. In circle zero cells like S. cerevisiae C468 it will remain as the B form, since it contains no intact flip gene.

DESCRIPTION OF THE PREFERRED EMBODIMENTS

A. Definitions

As used herein, "reference" protein refers to a protein of known amino acid sequence whose biological activity is also known, and which contains at least one methionine which becomes oxidized upon treatment with chloramine T. The protein may be from any source such as mammals, preferably human. It has been shown that chloramine T preferentially oxidizes, in native (non-denatured) proteins, only methionine residues which are exposed (Shechter, Y., et al., *Biochem.* (1975) 14:4497-4503). Treatment of peptides or of a denatured native protein, in at least some cases, can result in oxidation of all methionine residues to the sulfoxides. Oxidation of any available sulfhydryl groups to disulfide linkages may also occur. Treatment with hydrogen peroxide under appropriate conditions also results in conversion of methionine to methionine sulfoxide.

"Therapeutic protein" refers to a protein that is suitable for parenteral administration to humans or other mammals to provide therapy thereto or as a prophylactic agent. The adjective "therapeutic" includes having blocking activity, eliminating naturally occurring deficiencies in the protein or in the ability of the protein to act in the body, and combatting cancer or infectious diseases.

"Therapeutically useful," in relation to the biological activity of the muteins herein, refers to muteins that exhibit substantially the same or enhanced pharmacokinetic properties or specific activity compared to the reference protein. Thus, the mutein may have reduced specific activity, but still be therapeutically useful due to its advantageous pharmacokinetic properties. Different proteins are expected to have different pharmacokinetic and therapeutic properties that are advantageous for different routes of administration. A long-acting drug might only be administered every 3-4 days, every week, or once every two weeks.

"Oxidation-resistant mutein," in relation to the "reference" protein, refers to a related amino acid sequence which has a biological activity substantially the same as the reference protein. However, it contains a conservative amino acid substitution for any methionine residue which is particularly susceptible to oxidation by chloramine T or hydrogen peroxide. Such substitutions are not intended to render the mutein resistant to all oxidations, such as beneficial oxidations which might include creation of a disulfide linkage required for full activity.

A methionine "susceptible to oxidation by chloramine T or peroxide" refers to a methionine which undergoes, among all the methionines present, the most rapid conversion to the sulfoxide in the presence of either of these reagents under the conditions specified below. For treatment with either reagent the protein is dissolved in buffer, 50 mM Tris-HCl, pH 8.0, for chloramine T, 50 mM sodium phosphate, pH 6.8 for peroxide, at a concentration of about 0.2 mg/ml. For some recombinantly produced proteins, solubilizing agents, e.g., 0.1% detergent, may be required to effect solubility. For chloramine T, the oxidant is added to a two-fold molar excess, and the reaction incubated for up to 15 minutes at 25° C. For peroxide, $H_2O_2$ is added to 30 mM and the reaction incubated for up to one hour at 25° C. Chloramine T oxidation and hydrogen peroxide oxidation exhibit overlapping specificities with respect to methionine. Significant (at least 50%) oxidation with respect to either of these reagents under the above specified conditions defines a methionine residue as "susceptible" for purposes herein.

A "non-susceptible" methionyl residue is defined as a methionyl residue which is oxidizable, but is oxidized at a slower rate than the "susceptible" methionyl residue. The methionines in proteins have variable susceptibility to oxidation, and the preferred embodiments have the most susceptible methionine(s) replaced. The degree of susceptibility and the number of methionines to be replaced will depend on the preparation. If it is possible to make the protein more homogeneous without further methionine substitutions, then only the most susceptible methionine(s) will be replaced because it is desirable to keep the protein sequence as close to the native protein sequence as possible.

A "conservative" amino acid alteration is defined as one which does not adversely affect biological activity. Conservative amino acid substitutions for oxidizable methionines, according to the invention, are selected from the neutral or non-polar amino acids, particularly those with favorable steric and hydrophobic properties. Preferred are glycine, alanine, serine, threonine, valine, isoleucine, leucine, asparagine, glutamine, tyrosine, and phenylalanine. More preferred are alanine, serine, threonine, valine, leucine, and isoleucine. Even more preferred are alanine, serine, leucine, glutamate, and valine, and most preferred is alanine.

It should be noted that mouse IL-2, which shares 65% amino acid homology with human IL-2 overall and including the region near residue 104, has a glutamic acid substitution for methionine at position 104. Fiers, W. et al., in *Cellular and Molecular Biology of Lymphokines*, C. Sorg and A. Schimpl. editors, pp. 595–603, Academic Press, 1985. There is no nearby methionine in the mouse sequence, suggesting that methionine is not required at or near residue 104 for activity and that glutamic acid may also be considered a conservative substitution for residue 104 in the human sequence.

The relationship, therefore, of the "reference" protein to the oxidation-resistant mutein is that of identical amino acid sequence except for substitution of a conservative amino acid for the susceptible methionine, or the deletion thereof.

"Recombinant host cells", "host cells", "cells", "cell cultures", and so forth are used interchangeably, and designate individual cells, cell lines, cell cultures and harvested cells which have been, or are intended to be, transformed with the recombinant vectors of the invention. These terms also include the progeny of the cells originally receiving the vector. It is well understood that not all of the progeny of a single cell are precisely, necessarily identical with the parent, due to spontaneous or intentional mutations or alterations in the culture conditions. These progeny are also included in the definition, so long as the capacity to perform the function of producing the oxidation-resistant mutein of the invention conferred by the vector is retained.

"Transformed" refers to any process for altering the DNA content of the host, including in vitro transformation procedures as described below, phase infection, or such other means for effecting controlled DNA uptake as are known in the art.

"Operably linked" as used herein regarding DNA sequences or genes refers to the situation wherein the sequences or genes are juxtaposed in such a manner as to permit their ordinary functionality. For example, a promoter operably linked to a coding sequence refers to those linkages where the promoter is capable of controlling the expression of the sequence.

The expression "control sequences" refers to DNA sequences which control the expression of the sequence which encodes the oxidation-resistant mutein. Examples include promoters for transcription initiation, optionally with an operator, enhancer regions, ribosome binding site sequences, and translation signals which initiate and terminate translation of the gene. Such control sequences must be compatible with, i.e., operable in, the host into which they will be inserted.

"Inert, non-allergenic, pharmaceutically compatible carrier" refers to a carrier for the mutein herein which does not react with the mutein, is water soluble and preferably non-sensitive to water, is itself stable, does not elicit an allergic response in a recipient, and is compatible with the mutein physiologically and pharmaceutically so that a stable, soluble formulation is made. The carrier may be liquid or solid and if solid, may be a solid bulking agent for pharmaceutical tablet formulation.

B. General Description

To obtain the oxidation-resistant muteins of the invention, a reference protein is identified which exhibits preferential oxidation of a specific methionyl residue and this residue is replaced by a conservative amino acid substitution. The invention is applied to proteins wherein this residue is known. Where the location of this residue is not known, it can be determined by any of several means known in the art.

For example, RP-HPLC in some instances will be adequate to resolve preference protein from reference protein which contains methionyl sulfoxide. The protein is subjected to analysis on RP-HPLC before and after treating with. e.g., chloramine T under the specific conditions set forth in A above. (Alternatively, peroxide could be used.) Conditions are selected whereby only the most susceptible methionyl residues are oxidized to the sulfoxide. Both the major peak resulting from chloramine T oxidation, and the major peak obtained without such oxidation, are subjected to procedures designed to determine the position of any methionyl residue which has undergone oxidation.

A variety of procedures for identifying methionine sulfoxides can be used. However, a particularly convenient procedure for proteins with a small number of methionines utilizes cyanogen bromide cleavage (which reagent cleaves at methionyl residues, but is unreactive when those methionyl residues are oxidized), followed by HPLC peptide mapping and sequence analysis.

The cyanogen bromide cleavage mixture is first reduced with, for example, dithioerythritol to destroy any disulfide linkages remaining. For the reference protein, untreated with chloramine T, the number of peptides obtained should equal the number of internal methionine residues plus 1. For the protein oxidized by chloramine T, the number of resulting peptides will be diminished in proportion to the number of internal methionines oxidized. Thus, a comparison of the number of peptides obtained upon treatment by cyanogen bromide cleavage, DTE reduction, and HPLC analysis will permit a conclusion as to the number of internal methionyl residues present, and the number which are exposed for oxidation by chloramine T. Sequencing of the peptides thus obtained, along with, for example, comparision to the complete amino acid sequence independently established, will then reveal the location of the oxidized methionine with respect to the complete sequence.

After the location of the susceptible methionine is established, the protein is altered by site-specific mutagenesis of the sequence encoding the protein. DNA coding sequences for a large number of proteins, such as interleukin-2, interferon-$\alpha_a$, -$\beta$, and -$\gamma$, human growth hormone, tissue plasminogen activator, colony stimulating factors (CSF-1, CSF-G, etc.), urokinase, and many others, area already known and available in the art. Coding sequences not known or available in the art may be obtained by conventional methods such as sequencing probe-specific clones from cDNA libraries prepared from messenger RNA isolated from cells which produce the desired protein.

To prepare an oxidation-resistant mutein of the reference protein, a DNA sequence encoding the reference protein, cloned into a convenient M-13 cloning vector, is subjected to site-specific mutagenesis using the appropriate primer to convert the residue at the identified position from methionine to a conservative amino acid replacement. Site-specific (or primer-directed) mutagenesis is now a technique which is well-established in the art. Briefly, a synthetic oligonucleotide complementary to the desired sequence is used as a primer in the synthesis of a strand complementary to the phase single-stranded reference sequence. The resulting double-stranded DNA is transformed into a phase-supporting host bacterium. Cultures of the transformed bacteria are plated in top agar, permitting plaque formation from single cells which harbor the phage. Theoretically, 50% of the plaques will consist of phase containing the mutated form; 50% will have the original sequence. The plaques are hybridized with kinased synthetic primer under stringency conditions which permit hybridization only with the desired sequence, which will form a perfect match with the probe. Hybridizing plaques are then picked and cultured, and the DNA is recovered.

The resulting DNA is then ligated into expression vectors using standard procedures, which can be precisely identical to those used in preparing expression vectors for the reference sequence. An oxidation-resistant mutein may then be produced in suitable hosts under the control of compatible control sequences using any of the recombinant host cell systems known in the art (see C.1). The methionine-replaced muteins thus produced are recovered and purified using standard protein purification techniques.

One protein purification technique if the protein is in the form of a refractile material produced from a microorganism host is to (a) disrupt the cell membrane of the host, (b) remove greater than 99% by weight of the salts from the disruptate, (c) redisrupt the desalted disruptate, (d) add a material to the disruptate such as sucrose to increase the density or viscosity of, or to create a density or viscosity gradient in, the liquid within the disruptate, and (e) separate the refractile material from the cellular debris by high-speed centrifugation of 10,000 to 40,000 × g. Preferably the sucrose is added to increase the density of the liquid to a P of between 1.13 and 1.17 g/cm³. Further details are provided in copending U.S. application Ser. No. 749,951 filed Jun. 26, 1985, the disclosure of which is incorporated herein by reference.

Alternatively, the cell membrane (for IL-2) may be disrupted and the disruptate is extracted with an aqueous solution of a chaotropic agent such as urea which extracts non-IL-2 proteins selectively from the cellular material and from the IL-2. Then the IL-2 is solubilized with a solubilizing agent such as SDS in the presence of a reducing agent to reduce the IL-2, the reduced IL-2 is then separated from the solution in the presence of the reducing agent, the IL-2 is then oxidized, purified by gel filtration or reverse-phase high performance liquid chromatography and recovered. This latter recovery process is more fully described in U.S. Pat. No. 4,569,790 issued Feb. 11, 1986 and incorporated herein by reference.

In a third embodiment, the first alternative is employed to isolate the refractile bodies and then the second alternative is employed to dissolve the refractile bodies in a solubilizing agent such as SDS in the presence of the reducing agent and separating, oxidizing and purifying as described above.

Oxidation of proteins such as IL-2 or IFN-$\beta$ during the recovery step may be carried out by using iodosobenzoic acid, as described by U.S. Pat. No. 4,530,787, or by using a copper ion, as described by U.S. Pat. No. 4,572,798 issued Feb. 25, 1986, the disclosures of which are incorporated herein by reference.

The oxidation-resistant preparations have similar biological activity to that of the pertinent reference protein, and therefore will be in the same applications.

The following embodiments describe use of human proteins for veterinary or human use, although the present invention may find utility for proteins from other mammalian species or for human proteins for other uses. For example, proteins from such mammals as, e.g., mice, rats, rabbits or primates may be used for therapeutic treatment of mammals, including humans. In addition, mammalian proteins may find agricultural uses.

B.1. One Preferred Embodiment—IL-2 Oxidation-Resistant Muteins

The method of the invention is illustrated in one aspect by its application to interleukin-2, a lymphokine which is secreted from induced peripheral blood lymphocytes, or from Jurkat cells, as described by Taniguchi, T., et al., *Nature* (1983) 24:305.

Recombinant production of IL-2 has been reported by a number of groups. As shown in FIG. 1, mature, native IL-2 has a 133 amino acid sequence containing alanine at position 1, three cysteines (at positions 58, 105, and 125), and four methionine residues (at positions 23, 38, 46, and 104). Designation of various forms of IL-2 herein is made with respect to the sequence shown and numbered as in FIG. 1, noting only modifications thereof at the subscripted positions. Thus, the identical sequence, but missing the N-terminal alanine, is designated des-ala$_1$ IL-2; the same sequence but with a serine residue at position 125 (instead of cysteine as shown) is designated ser$_{125}$ IL-2.

In addition to native IL-2, recombinant forms of IL-2 which contain certain modifications in amino acid structure have been shown to be comparably active to the native sequence. For example, recombinant IL-2 lacking the five N-terminal amino acids, including the glycosylation site at position 3, has significant biological activity (Japanese Patent Application No. 235,638 filed Dec. 13, 1983, the disclosure of which is incorporated herein by reference). U.S. Pat. No. 4,518,584 issued May 21, 1985, and incorporated herein by reference, discloses a preferred modification of the N-terminal sequence with the alanyl residue at position 1 deleted. Also disclosed are IL-2 muteins with a neutral amino acid residue such as serine, alanine, threonine or valine at position 125 instead of cysteiene. These muteins have superior predictability with respect to disulfide linkage formation. Alternative conservative amino acid replacements at position 125, notably alanine or valine, are also disclosed. The applicants have found that both the $ser_{125}$ IL-2 and $ala_{125}$ IL-2 are fully active in cell proliferation assays. (Replacement of the cysteine residues at position 58 or 105 results in a loss of activity, since these residues are participants in the necessary disulfide link of the native molecule.)

Recombinant forms of IL-2 prepared for clinical testing have been shown to contain minor amounts of contaminants using analytical techniques with higher resolution than the preparative purification procedures used to manufacture the clinical samples. Both for proteins in general, and for IL-2 in particular, one cause for production of contaminants during purification, due to alteration of three-dimensional structure or formation of complexes, resides in the ability of certain free sulfhydryl groups to form disulfides other than those present in the active form of the protein. Accordingly, purification procedures for IL-2 are conducted under conditions which maintain cysteine residues in the sulfhydryl condition prior to permitting disulfide bond formation under controlled conditions of moderate oxidation. Nevertheless, it has now been found that because equipment and reagents used in purification procedures for pharmaceutical proteins must be sterile, residual oxidants, such as hydrogen peroxide, from sterilizing wash solutions may be present in sufficient amounts to cause oxidative conversions in the IL-2 preparations. Furthermore, such oxidations may also occur on storage.

All of the above-mentioned forms of IL-2 may be used as the reference protein in this preferred embodiment which is designed to delete or substitute a conservative amino acid for the methionine residue susceptible to such oxidation. Oxidation-resistant muteins may be valuable in providing compositions which retain potency as protein products, or oxidation resistance may alter the pharmacological behavior of the molecules in other beneficial ways.

Activity for the oxidation-resistant IL-2 mutein is verified using the standard HT-2 cell bioassay, as set forth by Watson, J., *J. Exp. Med.* (1979) 150:1507–1519 and by Gillis, S., et al., *J. Immunol.* (1978) 120:2027–2032. The mutein is also equally effective at activating NK cells in vitro as the reference molecule.

The oxidation-resistant IL-2 mutein may be recovered from an RP-HPLC pool, obtained as described in §B, by precipitating it from the pool (which may consist of acidic propanol), neutralizing the pH as by adding base, thereby obtaining a precipitate, centrifuging, redissolving the centrifugate in a non-toxic solubilizer such as SDS, and using S-200 gel filtration to remove oligomers if necessary. When SDS is used as solubilizer, the SDS is reduced at the final formulation stage to a level of about 100 to 250, preferably approximately 200, $\mu g/mg$ IL-2, by diafiltration using an appropriate buffer.

Following diafiltration, the IL-2 concentration is readjusted to a concentration in the range of about 0.01 to 2 mg/ml and the IL-2 may be formulated in a non-toxic, non-allergenic, pharmaceutically compatible carrier medium such as distilled water, Ringer's solution, Hank's solution, or physiological saline. A water-soluble carrier may be added to the desired level. The carrier will typically be added such that it is present in the solution at about 1 to 10% by weight, preferably about 5% by weight. The exact amount of carrier added is not critical. Conventional solid bulking agents which are used in pharmaceutical tablet formulation may be used as the carrier. These materials are water soluble, do not react with the IL-2, and are themselves stable. They are also preferably non-sensitive (i.e., nonhygroscopic) to water. Examples of carriers that may be added are non-toxic stabilizers such as mannitol or other materials such as lactose and other reduced sugars such as sorbitol, starches and starch hydrolysates derived from wheat, corn, rice, and potato, microcrystalline celluloses, and albumin such as homologous serum albumin. Mannitol is preferred.

The carrier adds bulk to the formulation such that when unit dosage amounts of the solution are lyophilized in containers, such as sterile vials, the freeze-dried residue will be clearly discernible to the naked eye. In this regard the preferred carrier, mannitol, yields an aesthetically acceptable (white, crystalline) residue which is not sensitive to water. The nonsensitivity of mannitol to water may enhance the stability of the formulation.

After the carrier is added, the unit dosage amounts (i.e., volumes that will provide 0.01 to 2 mg, preferably 0.2 to 0.3 mg, IL-2 per dose) of the solution are dispensed into containers, the containers are capped with a slotted stopper, and the contents are lyophilized using conventional freeze-drying conditions and apparatus.

The lyophilized, sterile product consists of a mixture of (1) recombinant IL-2, (2) carrier (mannitol), (3) detergent (SDS), and (4) a small amount of buffer which will provide a physiological pH when the mixture is reconstituted. The recombinant IL-2 will typically constitute about 0.015% to 3.85% by weight of the mixture, more preferably about 0.4% to 0.6% of the mixture. Storage tests of this product indicate that the IL-2 is stable in this form for more than three months at 2° C. to 8° C.

The lyophilized mixture may be reconstituted by injecting a conventional parenteral aqueous injection such as water for injection, Ringer's injection, dextrose injection, dextrose and salt injection, or the like, into the vial. The injection should be added against the side of the vial to avoid excess foaming. The amount of injection added to the vial will typically be in the range of 1 to 5 ml, preferably 1 to 2 ml.

Administration of the IL-2 muteins to humans or animals may be, for example, intraveneous, intraperitoneal, intramuscular, or subcutaneous as deemed appropriate by the physician. The amount of IL-2 mutein administered will usually range between about $1 \times 10^4$ and $2 \times 10^8$ units, depending on the subject and its weight.

The IL-2 muteins herein are useful for the diagnosis and treatment (local or systemic) of bacterial, viral, parasitic, protozoan and fungal infections; for augmenting cell-mediated cytotoxicity; for stimulating lymphokine-activated killer cell activity; for mediating recovery of immune function of lymphocytes; for augmenting alloantigen responsiveness; for facilitating recovery of immune function in acquired immune-deficient states; for reconstitution of normal immunofunction in aged humans and animals; in the development of diagnostic assays such as those employing enzyme amplification, radiolabeling, radioimaging, and other methods known in the art for monitoring IL-2 levels in the diseased state; for the promotion of T cell growth in vitro for therapeutic and diagnostic purposes; for blocking receptor sites for lymphokines; and in various other therapeutic, diagnostic and research applications.

Various therapeutic applications of human IL-2 have been investigated and reported by S. A. Rosenberg, and colleagues (see Mule, et al., *Science* (1984) 225:1487 and S. Rosenberg, et al., *New England Journal of Medicine* (1985) 313(23):1485-1492, for example). IL-2 muteins may be used by themselves or in combination with other immunologically relevant B or T cells or other therapeutic agents. Non-limiting examples of relevant cells are B or T cells, and natural killer cells; and exemplary therapeutic reagents which may be used in combination with the polypeptides of this invention are the various interferons, especially alpha-, beta-, and gamma-interferon, B cell growth factor, CSF-1, interleukin-1, or tumor necrosis factor.

B.2 A Second Preferred Embodiment—IFN-β Oxidation-Resistant Muteins

A similar oxidation sensitivity exists with respect to β-interferon (IFN-β). The 166 amino acid sequence of mature, native IFN-β is shown in FIG. 2. There are three cysteine residues, at positions 17, 31, and 141. The cysteine residue at position 17 has been shown not to be essential for biological activity, and IFN-β muteins with conservative amino acid substitutions at position 17 have been disclosed in U.S. Pat. No. 4,518,584 issued May 21, 1985, and incorporated herein by reference. It has been concluded that the disulfide bridge found in both the native and mutated forms of IFN-β is between the cysteine at position 141 and that at position 31. In addition, the IFN-β sequence, as shown in FIG. 2, contains four methionyl residues (at positions 1, 36, 62, and 117). Purification procedures performed on $ser_{17}$ IFN-β result in products which give similar patterns on RP-HPLC analysis to those obtained from purified clinical product IL-2. Oxidation of IFN-β with hydrogen peroxide, using conditions described above, has similar effects on the RP-HPLC patterns as observed for IL-2. The biological activity of IFN-β where at least the methionine at position 62 is oxidized is 1-5% of the activity of the non-oxidized counterpart. Mutein forms of IFN-β with a methionine at position 36, 62 or 117 replaced may be obtained through site-specific mutagenesis. The muteins may then be oxidized and the RP-HPLC results analyzed for the presence of peaks characteristic of oxidized forms. The various species may then be analyzed to determine the location of the oxidized methionine.

After site-specific mutagenesis, an expression clone is prepared containing a promoter, the IFN-β mutein-encoding gene, and an appropriate expression vector. Suitable cells are transformed with the clone and grown in a fermentation medium or in a shaker flask.

The interferon-β mutein is recovered from the culture in which the transformed cells are grown by disrupting the cells, typically by homogenization or sonication. The cells may be concentrated prior to disruption, by, for example, diafiltration.

The cellular debris is then treated with one or more solubilizing agents such as SDS and dithiothreitol for a period of about one hour. The resulting cell suspension is then extracted with one or more extractants, such as 2-butanol, to isolate the crude interferon-β, usually using a 1:1 2-butanol:suspension volume ratio in a static mixer as described in U.S. Pat. No. 4,450,103 issued May 22, 1984. The mixture is then centrifuged and the extractant-rich, organic phase is collected.

To the organic phase, adjusted to a pH of about 6-8, preferably about 6.2, is added a precipitating solution containing salts and, for example, SDS. The resulting suspension is centrifuged and the interferon-rich pellet is suspended in a solution, e.g., containing SDS. Then o-iodosobenzoic acid or cupric chloride is added to promote the formation of disulfide bonds as described in U.S. Pat. Nos. 4,530,787 and 4,572,798, respectively.

After the reaction, the IFN-β is purified on a preparative RP-HPLC column, and subjected to analytical RP-HPLC to purify further and to characterize the product.

The interferon product can then be assayed for antiviral activity using the yield reduction assay described by Steward and Lockhart, *J. of Virol.*, 6:795-799 (1970) or the cytopathic effect assay described by Steward, W. E. II, *The Interferon System* (New York:Springer-Verlag, 1981), p.17.

The interferon may then be formulated in the same manner as native IFN-β. For therapeutic or diagnostic applications, it may be formulated in non-toxic, non-allergenic, pharmaceutically compatible carrier media such as distilled water, Ringer's solution, Hank's solution, or physiological saline. The formulation may also contain non-toxic stabilizers such as dextrose and non-toxic solubilizers such as albumin. Administration of the IFN-β muteins to humans or animals may be, for example, intravenous, intraperitoneal, intramuscular, or subcutaneous as deemed appropriate by the physician. The amount of IFN-β mutein administered will usually range between about $1 \times 10^4$ and $2 \times 10^8$ units, depending on the subject and its weight.

The IFN-β mutein may be formulated as described for the IL-2 mutein, including modification by means of an activated homopolymer such as polyethylene glycol.

When purified and formulated as described above, the IFN-β mutein with alanine substituted at position 62 was found to be oxidation-resistant and had approximately 13% of the antiviral specific biological activity of the native-sequence IFN-β. Other amino acid substitutions at position 62 may be expected to have different levels of IFN-β activity.

The IFN-β muteins may be useful as anti-viral, anti-psoriatic, anti-proliferative, immunomodulatory and anti-tumor agents.

C. Standard Methods

Most of the techniques which are used to transform cells, construct vectors, effect hybridization with probe, and the like are widely practiced in the art, and most practitioners are familiar with the standard resource materials which described specific conditions and procedures. However, for convenience, the following paragraphs may serve as a guideline.

C.1. Hosts and Control Sequences

The method herein is not limited to the particular host or control sequence employed. Either procaryotic or eucaryotic hosts may be used for expression of DNA sequences; cloning of such sequences generally employs procaryotes for convenience. Procaryotes most frequently are represented by various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid from an *E. coli* species by Bolivar, et al., *Gene* (1977) 2:95. pBR33 contains genes for ampicillin and tetracycline resistance, and thus provides additional markers which can be either retained or destroyed in constructing the desired vector. Commonly used procaryotic control sequences include such commonly used promoters as the beta-lactamase (penicillinase) and lactose (lac) promoter systems (Chang, et al., *Nature* (1977) 198:1056) and the tryptophan (trp) promoter system (Goeddel, et al., *Nucleic Acids Res.* (1980) 8:4057) and the lambda derived $P_L$ promoter and N-gene ribosome binding site (Shimatake, et al., *Nature* (1981) 292:128), which has been made useful as a portable control cassette, as set forth in copending U.S. application Ser. No. 685,312, filed Dec. 24, 1984, the disclosure of which is incorporated herein by reference. However, any available promoter system compatible with procaryotes can be used.

In addition to bacteria, eucaryotic microbes, such as yeast, and Asperigillus, may also be used as hosts. Laboratory strains of *Saccharomyces cerevisiae*, Baker's yeast, are most used, although a number of other strains are commonly available. Plasmid vectors suitable for yeast expression include use of the 2 micron origin of replication (Broach, J. F., *Meth. Enz.* (1983) 101:307), and those described by, for example, Stinchcomb, et al., *Nature* (1979) 282:39, Tschempe, et al., *Gene* (1980) 10:157 and Clarke, L., et al., *Meth. Enz.* (1983) 101:300). Control sequences for yeast vectors include promoters for the synthesis of glycolytic enzymes (Hess, et al., *J. Adv. Enzyme Reg.* (1968) 7:149; Holland, et al., *Biochemistry* (1978) 17:4900). Additional promoters known in the art include the promoter for 3-phosphoglycerate kinase (Hitzeman, et al., *J. Biol. Chem.* (1980) 255:2073), as well as those for other glycolytic enzymes. Other promoters are available such as the promoter regions of alcohol dehydrogenase 2, isocytochrome C, acid phosphatase, degradative enzymes associated with nitrogen metabolism, and enzymes responsible for maltose and galactose utilization. It is also believed that terminator sequences are desirable at the 3' end of the coding sequences. Such terminators are found in the 3' untranslated region following the coding sequences in yeast-derived genes such as those derived from the enolase gene containing plasmid peno46 (Holland, M. J., et al., *J. Biol. Chem.* (1981) 256:1385) or the LEU2 gene obtained from YEp13 (Broach, J., et al., *Gene* (1978) 8:121).

The advantages of using yeast as a host for IL-2 production are: (1) a homogeneous, native N-terminus (alanine) is achieved, (2) the protein contains three cysteines as does the native protein, (3) the protein does not need to be chemically treated in vitro to form the 58 to 105 disulfide bond, because it is secreted in a fully active disulfide-bonded form, and (4) the protein may be more soluble than the corresponding recombinant IL-2 produced in *E. coli*.

It is also, of course, possible to express genes encoding polypeptides in non-human eucaryotic host cell cultures derived from multicellular organisms. See, for example, *Tissue Cultures*, Academic Press, Cruz and Patterson, editors (1973). Useful host cell lines include VERO, CV-1, COS-7, HeLa cells, Chinese hamster ovary (CHO) cells, Aspergillus or insect cells using a baculovirus expression vector, the latter being described in EP Publication 127,839 published Dec. 12, 1984. Expression vectors for such cells ordinarily include promoters and control sequences compatible with mammalian cells such as, for example, the commonly used early and late promoters from Simian Virus 40 (SV 40) (Fiers, et al., *Nature* (1978) 273:113), or other viral promoters such as those derived from polyoma, Andenovirus 2, bovine pepilloma virus, or avian sarcoma viruses. General aspects of mammalian cell host system transformations have been described by Axel; U.S. Pat. No. 4,399,216 issued Aug. 16, 1983. It now appears, also, that "enhancer" regions are important in optimizing expression; these are, generally, sequences found upstream or downstream of the promoter region in non-coding DNA regions. Origins of replication may be obtained, if needed, from viral sources. Plant cells are also now available as hosts, and control sequences compatible with plant cells such as the nopaline synthase promoter and polyadenylation signal sequences (Depicker, A., et al., *J. Mol. Appl. Gen.* (1982) 1:561) are available.

C.2 Transformations

Depending on the host cell used, transformation is done using standard techniques appropriate to such cells. The calcium treatment employing calcium chloride, as described by Cohen, S. N., *Proc. Natl. Acad. Sci. (USA)* (1972) 69:2110, or the $RbCl_2$ method described in Maniatis, et al., *Molecular Cloning: A Laboratory Manual* (1982) Cold Spring Harbor Press, p. 254 is useful for procaryotes or other cells which contain substantial cell wall barriers. Infection with *Agrobacterium Tumefaciens* (Shaw, C. H., et al., *Gene* (1983) 23:315) is used for certain plant cells. For mammalian cells without such cell walls, the calcium phosphate precipitation method of Graham and van der Eb, *Virology* (1978) 52:546 is preferred. Transformations into yeast are carried out according to the method of Van Solingen, P., et al., *J. Bact.* (1977) 130:946, Hsiao, C. L., et al., *Proc. Natl. Acad. Sci. (USA)* (1979) 76:3829, and Klebe, R. J. et al., *Gene* (1983) 25:333. Transformation into insect cells may be accomplished using a baculovirus expression vector as described in EP 127,839, supra.

C.3 Probing cDNA or Genomic Libraries cDNA or genomic libraries may be probed in accordance with the procedure described by T. Maniatis et al., *Molecular Cloning-A Laboratory Manual* (Cold Spring Harbor Laboratories, 1982).

C.4 Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs Product Catalog. In general, about 1 $\mu$g of plasmid or DNA sequence is cleaved by one unit of enzyme in about 20 $\mu$l of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol followed by running over a Sephadex G-50 spin column. If desired, size separation of the cleaved fragments may be performed by polyacrylamide gel or agarose gel electrophoresis using standard techniques. A general description of size separations is found in *Methods in Enzymology* (1980) 65:499-560.

Restriction-cleaved fragments may be blunt ended by treating with the large fragment of *E. coli* DNA polymerase I (Klenow) in the presence of the four deoxyribonucleoside triphosphates (dNTPs) using incubation times of about 15 to 25 minutes at 20° to 25° C. in 50 mM Tris pH 7.6, 50 mM NaCl, 6 mM MgCl$_2$, 6 mM DTT and 5-10 $\mu$M dNTPs. The Klenow fragment either fills in at 5' sticky ends or chews back protruding 3' single strands. If desired, selective repair of protruding 5' ends can be performed by supplying selected dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides are prepared by the triester method of Matteucci, et al., (*J. Am. Chem. Soc.* (1981) 103:3185) or more conventionally using the appropriate chemistry for commercially available automated oligonucleotide synthesizers. Kinasing of single strands prior to annealing or for labeling is achieved using the process of Maniatis et al., supra.

Ligations are typically performed in 10-30 $\mu$l volumes under the following standard conditions and temperatures: 20 mM Tris-Cl pH 7.5, 10 mM MgCl$_2$, 10 mM DTT, 33 $\mu$g/ml BSA, 10 mM-50 mM Nacl, and either 40 $\mu$M ATP, 0.01-0.02 (Weiss) units T4 DNA ligase (for "sticky end" ligation) or the 1 mM ATP, 0.3-0.6 (Weiss) units T4 DNA ligase (for "blunt end" ligation). Many variations are known to those skilled in the art. Intermolecular "stick end" ligations are usually performed at 33-100 $\mu$g/ml total DNA concentrations (5-100 nM total end concentration). Intermolecular blunt end ligations (usually employing a 1-20 fold molar excess of linkers) are performed at 1 $\mu$M total ends concentration.

In vector construction employing "vector fragments", the vector fragment is commonly treated with bacterial alkaline phosphatase (BAP) or calf intestinal alkaline phosphatase (CIAP) in order to remove the 5' phosphate and prevent religation of the vector. BAP digestions are conducted at pH 8 in approximately 150 mM Tris, in the presence of NA$^+$ and Mg$^{+2}$ using about 1 unit of BAP per $\mu$g of vector at 60° C. for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

C.5 Verification of Construction

In the constructions set forth below, correct ligations for plasmid construction are confirmed by first transforming *E. coli* strain MM294 obtained from *E. coli* Genetic Stock Center, CGSC #6135, or other suitable host, with the ligation mixture. Successful transformants are selected by ampicillin, tetracycline or other antibiotic resistance or using other markers depending on the mode of plasmid construction, as it understood in the art. Plasmids from the transformants are then prepared according to the method of Clewell, D. B., et al., *Proc. Natl. Acad. Sci.* (*USA*) (1969) 62:1159, optionally following chloramphenicol amplification (Clewell, D. B., *J. Bacteriol.* (1972) 110:667). The isolated DNA is analyzed by restriction enzyme analysis and/or the DNA is sequenced by the dideoxy method of Sanger, F., et al., *Proc. Natl. Acad. Sci.* (*USA*) (1977) 74:5463 as further described by Messing, et al., *Nucleic Acids Res.* (1981) 9:309, or by the method of Maxam, et al., *Methods in Enzymology* (1980) 65:499.

C.6 Hosts Exemplified

Host strains used in cloning and expression herein are as follows:

For cloning and sequencing, and for expression of construction under control of most bacterial promoters, *E. coli* strain MM294 (supra) or derivatives, Talmadge, K., et al., *Gene* (1980) 12:235; Meselson, M., et al., *Nature* (1968) 217:1110, were used as the host.

For M13 phage recombinants, *E. coli* strains susceptible to phase infection, such as *E. coli* K12, DG98, are employed. The DG98 strain has been deposited with ATCC on Jul. 13, 1984 and has accession number 39,768. For yeast transformations, *S. cerevisiae* strains such as C468 (Innis, M. A. et al., *Science* (1985) 228:21-26) and its cir° derivative were used. C468 cir° was deposited with ATCC on Dec. 13, 1985 and has ATCC Accession No. 20,787. For expression of IFN-$\beta$ muteins in *E. coli*, strains may be used such as MM294, which has been deposited with ATCC on Feb. 14, 1984 and has ATCC Accession No. 39,607.

In the examples which follow, all temperatures are provided in degrees Celsius and all parts and percentages are weight, unless otherwise indicated. These examples are meant only to typify the procedure, and are not to be construed as limiting. Therefore, other reference forms IL-2 and IFN-$\beta$ or other proteins may be used, and other expression systems may be used to provide the protein. For example, a yeast construct can be designed to result in an intracellular yeast product lacking the leader sequence described herein. As stated above, desired coding sequences may be expressed in a variety of procaryotic and eucaryotic host systems using known control sequences.

EXAMPLES

D. Expression of Des-ala$_1$ Ala$_{104}$ Ser$_{125}$ IL-2 in *E. coli*

The following specific example is used to illustrate the application of the process of the invention to a particular active form of IL-2 as reference protein. In this example, the resulting coding sequence having the appropriate substitution to generate an alanine codon at position 104 in place of that for methionine is ligated into an expression vector utilizing the trp promoter system and the resulting vector is used to produce the desired protein in *E. coli*. (Des-ala$_1$ designates that the alanine at the 1 position of IL-2 has been deleted.)

D.1. Identification of Methionine Residues in IL-2 Preferentially Susceptible to Chloramine T The IL-2 mutein, des-ala$_2$ser$_{125}$ IL-2, was used as reference protein. This protein was prepared and purified to apparent homogeneity using preparative scale techniques, but was found to be heterogeneous when more sensitive analytical methods were applied. Analysis of the various species permitted identification of methionine 104 in IL-2 as the susceptible residue whose conversion to the sulfoxide accounts for much of the heterogeneity in the final product.

D.1.a Preparation of Reference IL-2 in *E. coli*

Des-ala$_1$ser$_{125}$ IL-2 is a biologically active mutein which contains the four methionine residues of the native sequence. This mutein, described by Wang et al., (1984) *Science*, 224, 1431-1433, was prepared from *E. coli* K12 strain MM294 transformed with pLW45, an expression vector containing the coding sequence for this protein under control of the trp promoter. This transformed strain was deposited in the American Type Culture Collection on Mar. 6, 1984, and has ATCC Accession No. 39,626.

*E. coli* transformed with pLW45 were grown as follows:

| | |
|---|---|
| (NH$_4$)$_2$SO$_4$ | 150 mM |
| KH$_2$PO$_4$ | 21.6 mM |
| Na$_3$ Citrate | 1.5 mM |
| ZnSO$_4$.7 H$_2$O | 30 μM |
| MnSO$_4$.H$_2$O | 30 μM |
| CuSO$_4$.5 H$_2$O | 1 μM |

The pH was adjusted to 6.50 with 2.5 N NaOH and the mixture autoclaved.

Under sterile conditions (post autoclave), the following were added to give final concentrations as shown:

| | |
|---|---|
| MgSO$_4$ | 3 mM |
| FeSO$_4$ | 100 μM |
| L-tryptophan | 14 mg/l |
| Thiamine-HCl | 20 mg/l |
| Glucose | 5 g/l |
| Tetracycline | 5 mg/l |
| Ethanol | 2% |
| Casamino acids | 2% |

Dow Corning Antifoam, polypropylene glycol (20% solution), glucose (50% solution), and KOG (5N), were added on demand, and the culture was maintained in a fermenter.

The pH of the fermenter was maintained at 6.8 with 5N KOH. Residual glucose was maintained between 5-10 g/l, dissolved oxygen at 40%, and temperature at 37±1° C. The casamino acids (20% stock solution) to a concentration of 2% were added when the OD$_{680}$ was about 10. Harvest was made three hours after the OD reached about 20.

D.1. b. Purification of the Reference Protein

The cells were lysed, and the IL-2 mutein was purified substantially as described in U.S. Pat. No. 4,569,790 issued Feb.11, 1986, assigned to the same assignee, and incorporated herein by reference.

Briefly, the harvested cells were concentrated, for example, by hollow fiber filtration, and about 20-40 g of material was resuspended in 200 ml of 50 mM Tris/1 mM EDTA, pH 8.1-8.5, and centrifuged at 3000-4000 × g for 10 minutes. The pellet was resuspended in 200 ml of Tris/EDTA buffer at 4° C. and sonicated. The cell debris from the sonicate, which contains the desired protein, was recovered by centrifugation, and the pellet resuspended in 60 ml Tris/EDTA buffer at room temperature. An equal volume of 8 M urea in the same buffer was added over five minutes, while rapid stirring was maintained. After 15–30 minutes of continued slow stirring, the debris, which again contains the desired protein, was recovered by centrifugation at 12,000×g for 15 minutes. The urea-extracted pellet was resuspended in 9 ml of 50 mM sodium phosphate, pH 6.8, 1 mM EDTA, 10 mM DTT at 20° C.,; 1 ml 20% SDS was added to 2% final concentration, and the suspension was mixed vigorously for five minutes. The supernatant, which now contains the desired protein, was recovered after centrifugation at 12,000×g for 10 minutes at room temperature. The supernatant was heated to 40° C. for 15 minutes to assure complete reduction of the sulfhydryl groups.

The reduced SDS extract of the urea pellet was extracted with an equal volume of 2-butanol containing 1 mM DTT at room temperature. The organic phase, adjusted to pH 8.0, was added slowly to 0.1% SDS in 10 mM sodium phosphate, 2 mM DTT, ph 6, and stirred for 20 minutes to give a precipitate, which was recovered, suspended in 5% SDS in phosphate buffered saline, and reduced by heating as above. The resulting solution (adjusted to pH 5.5) was purified by gel filtration using a Sephacryl-200 column.

The solution was loaded onto a 2.6 cm×95 cm S-200 column run in 50 mM sodium acetate, pH 5.5, 1 mM EDTA, 2 mM DTT, 1% SDS. The fractions containing the highest concentration of IL-2 activity and the lowest contaminant concentration were pooled, concentrated, reduced, and oxidized using cupric chloride substantially as described in U.S. Pat. No. 4,572,798 issued Feb. 25, 1986, assigned to the same assignee and incorporated herein by reference. (The oxidation links the cysteine residues at positions 58 and 105 to the desired cystine linkage.) The oxidized protein was further purified by preparative RP-HPLC, and the IL-2 peak was pooled and lyophilized following addition of mannitol to 5%. The IL-2 protein was resuspended to the original volume in 50 mM sodium phosphate buffer (pH 6.8) containing 0.1% SDS and assayed for bioactivity (using the standard HT-2 cell proliferation assay), for protein content (Lowry) and purity (by RP-HPLC and by non-reducing SDS-PAGE). The specific bioactivity was equivalent to that of native Jurkat IL-2 (4×10$^6$ units/mg) and purity was over 95%.

D.1.c. Detection and Analysis of Sulfoxide-Containing Protein

When the oxidized des-ala$_1$ser$_{125}$ IL-2 from 0.1. b was subjected to analytical RP-HPLC, the results shown in FIG. 3*a* were obtained. The major IL-2-containing peak (Peak B) is preceded by a smaller peak (Peak A). The peak A material was shown also to be IL-2, except that it contains a methionine sulfoxide residue at position 104.

The correlation of Peak A with an oxidized methionine in IL-2 was confirmed by oxidizing the sample with chloramine T as described above, and subjecting the oxidized sample to analytical RP-HPLC. FIG. 3*a* shows the RP-HPLC before and FIG. 3*a* after chloramine T oxidation. FIG. 3*b* shows that essentially all of Peak B protein of FIG. 3a appears in the Peak A position following chloramine T treatment. This is consistent with the foregoing interpretation, based on the known specificity of chloramine T for methionine (Shechter, Y., et al., (supra)). Similar results were obtained in an analogous experiment, which substituted 30 mM hydrogen peroxide for chloramine T as the oxidizing agent. (See FIGS. 4a and 4b).

The methionine residues of a particular sequence will vary in susceptibility. The location of the susceptible methionine in IL-2 was obtained in two ways. In one approach, both Peaks A and B from a lot which contained a particularly large amount of Peak A were separated by purification on RP-HPLC, exposed to cyanogen bromide (which cleaves protein sequences at methionine, but not at methionine sulfoxide residues), and then examined by RP-HPLC protein mapping and amino acid analysis or by N-terminal sequence analysis of the entire digest. Approximately 400 µg of material from each RP-HPLC peak was dissolved in 1 ml of 70% formic acid containing 1 mg cyanogen bromide. After incubation for 16 hours in the dark, samples were diluted 10 fold with water, lyophilized, and redissolved in 1 ml 0.15 M Tris-HCl, pH 8.8, containing 1% SDS. Aliquots of 50 µl were examined by HPLC before and after reduction with dithioerythritol (DTE), which reduction was accomplished by adding 1 mg DTE and incubating for one hour at 85° C. Analysis of the results obtained showed that the methionines in Peak B IL-2 are essentially unmodified. In contrast, all of the IL-2 molecules in Peak A contained an oxidized form of methionine at position 104, and the remaining methionyl residues were substantially unmodified.

In a related experiment, a 4:1 mixture of peaks A and b from chloramine T treated reference IL-2 was cleaved with CNBr and sequenced. Again, the methionine at 104 was found to be the most rapidly oxidized methionine.

This was confirmed by analyzing tryptic digests of Peak A and Peak B proteins which were reduced in dithiothreitol (DTT) carboxymethylated using iodoacetate, and subjected to RP-HPLC. Results of this analysis also confirmed that Peak A protein was identical with Peak B protein, except for oxidation of the methionine at position 104.

D.2 Preparation of the Coding Sequence for Des-ala$_1$ Ala$_{104}$ Ser$_{125}$ IL-2 in *E. coli*

An ala$_{104}$ mutein of the des-ala$_1$ser$_{125}$ IL-2 of 0.1 was prepared by site-specific mutagenesis using an M13 cloned reference protein sequence, prepared substantially as described in U.S. Pat. No. 4,518,584 issued May 21, 1985, and incorporated herein by reference. Briefly, the IL-2 gene from the plasmid pLW1, which was deposited at the American Type Culture Collection on Aug. 4, 1983, and assigned ATCC No. 39,405, was cloned into M13mp9 to give M13-IL-2. M13-IL-2 was used to serve as a template for oligonucleotide-directed mutagenesis to convert the cysteine at position 125 to a serine residue. To this end, 40 pmoles of the oligonucleotide 5'-GATGATGCTCTGAGAAAAGGTAATC-3' was kinased under standard conditions for use as primer and probe. Ten pmoles of the kinased primer was hybridized to 2.6 µg of single-stranded (ss) M13-IL-2 DNA in 15 µl of a mixture containing 100 mM NaCl, 20 mM Tris-Hcl, pH 7.9, 20 mM MgCl$_2$, and 20 mM β-mercaptoethanol by heating at 67° C. for five minutes and 42° C. for 25 minutes. The annealed mixture was chilled on ice and adjusted to a final volume of 25 µl in a reaction mixture containing 0.5 mM of each dNTP, 17 mM Tris-HCl, pH 7.9, 17 mM MgCl$_2$, 83 mM NaCl, 17 mM β-mercaptoethanol, 5 units of DNA polymerase I, Klenow fragment, 0.5 mM ATP, and 2 units of T$_4$ DNA ligase, incubated at 37° C. for five hours. The reactions were terminated by heating to 80° C. and the reaction mixtures were used to transform competent JM103 cells, which were plated onto agar plates, and incubated overnight to obtain phage plaques. The plaques were probed using kinased primer using standard prehybridization and hybridization conditions at high stringency (42° C. for eight hours). A plaque which hybridized to primer was picked. This plaque was designated M13-LW46, and contains the coding sequence for des-ala$_1$-ser$_{125}$ IL-2.

M13-LW46 was subjected to site-specific mutagenesis in a precisely analogous process, but using the primer 5'-CAGCATACTCACACGCGAATGTTGTTTC-3'. This primer was complementary to a sequence wherein nucleotides 307 and 308 are GC, instead of AT, as in the reference sequence. The oligonucleotide was kinased, and used as primer and probe in site-specific mutagenesis and recovery of mutagenized phage as above.

One of the mutagenized M13-LW46 plaques which hybridized with probe was designated SDL23, picked, cultured, and used to prepare expression vector pSY3001.

D.3 Construction of pSY3001

RF-DNA from SDL23 was digested with HindIII and PstI and the insert fragments were purified from a 1% agarose gel. Similarly, pTRP3, a pBR322 derivative containing the trp promoter, (§0.8) was digested with HindIII and EcoRI; the small fragment containing trp promoter was purified on an agarose gel. The pBR233 vector was digested with EcoRI and PstI and the large fragment purified on an agarose gel. The purified vector fragment and trp promoter fragment were ligated with the IL-2 mutein encoding fragment, and the ligation mixture was transformed into competent *E. coli* K12 strain MM294, generating a Tet$^R$ phenotype. The plasmid DNA was isolated and correct construction of pSY3001 confirmed by restriction analysis and dideoxy sequencing.

D.4 Production and Purification of Des-ala$_1$-Ala$_{104}$Ser$_{125}$ IL-2

*E. coli* transformed with pSY3001 were then grown as described in 0.1. a above, and the desired oxidation-resistant mutein was purified and oxidized as described in 0.1. b, with the following exceptions: The reduced supernatant from the 2% SDS-extracted urea pellet was loaded onto a 2.6 cm × 95 cm G-100 column run in 50 mM sodium phosphate, pH 6.8, 1 mM EDTA, 1 mM DTT, 0.1% SDS. The fractions containing IL-2 activity and the lowest contaminant concentration were pooled and concentrated by ultrafiltration using an Amicon YM-5 membrane. To ensure that all molecules were reduced, DTT was added to 10 mM, and the sample was heated to 60° C. for 10 minutes. The sample was immediately desalted using a 0.9 cm × 20 cm G-25 column with 50 sodium phosphate (pH 7.0), 0.1% SDS. The resulting purified oxidation-resistant mutein was immediately oxidized to obtain the cystine linkage as described above and assayed for biological activity and purity in a manner similar to that used for the reference protein, with similar results.

The standard HT-2 cell bioassay (supra) was used to assess the biological activity of the purified material from the pSY3001-transformed cells. The specific activity of the oxidation-resistant mutein was approximately $4 \times 10^6$ units/mg, the same as that for the clinical grade des-ala$_1$ser$_{125}$ IL-2, or native IL-2 which was purified from peripheral blood lymphocytes or the Jurkat cell line. The oxidation-resistant mutein displayed the same biological activity as the reference IL-2 protein when stored in solution at 4° C. for two months. The mutein also showed the same specific activity as the reference protein in NK activation assays.

The course of purification of the oxidation-resistant mutein is shown in FIG. 5, and the purified oxidation-resistant mutein product is compared with the purified reference IL-2 protein obtained from pLW45 transformants.

D.5 Homogeneity and Activity of the IL-2 Oxidation-Resistant Mutein

The purified oxidation-resistant mutein purified from pSY3001 transformant as in D.4 was subjected to analytical RP-HPLC with the results shown in FIG. 3c. A single, symmetrical peak was obtained showing that the Peak A material which was obtained in similarly purified reference IL-2 had been eliminated. The RP-HPLC retention time of the mutein differs slightly from that of the reference protein, as has been observed for other IL-2 point mutations (Kunitani, et al., Fifth Int'l Symposium on HPLC of Proteins, Peptides and Polynucleotides, Toronto, Canada, Nov. 4–6, 1985). FIG. 3d shows the results of chloramine T treatment of this preparation conducted exactly as set forth above for the reference IL-2. As expected, no change in the RP-HPLC pattern was obtained for des-ala$_1$ala$_{104}$ser$_{125}$ IL-2, indicating that this mutein lacks the methionine residue preferentially susceptible to oxidation by chloramine T. CNBr cleavage and N-terminal sequencing of the mixture as described above revealed only the presence of some oxidation of the "non-susceptible" methionines.

FIGS. 4c and 4d show the corresponding results obtained when oxidation was carried out using hydrogen peroxide.

D.7 Other Oxidation-Resistant IL-2 Muteins in *E. coli*

The DNA sequence for native IL-2, des-ala$_1$ IL-2, and ser$_{125}$ IL-2, as well as the above-illustrated des-ala$_1$ser$_{125}$ IL-2, can be genetically modified using analogous methods, but substituting as starting materials for M13-LW46, the following: to prepare ala$_{104}$ IL-2, M13-LW32; to prepare des-ala$_1$ala$_{104}$ IL-2, M13-IL-2; to prepare ala$_{104}$ser$_{125}$ IL-2, an M13 vector prepared using pLW55, a plasmid containing the desired coding sequence, which was deposited at the American Type Culture Collection on Nov. 18, 1983, and bears ATCC accession no. 39,516. In addition, the DNA sequence for ala$_{125}$ IL-2 can be genetically modified using analogous methods. Ala$_{125}$ IL-2 has been prepared and purified and shown to be fully active in biological assays.

These starting materials are described in detail in U.S. Pat. No. 4,518,584 (supra).

D.8 Construction of pTRP3

To construct the host vector containing the trp control sequences behind a HindII site, the trp promoter/operator/ribosome binding site sequence, lacking the attenuator region, was derived from pVH153, obtained from C. Yanofsky, Stanford University. Trp sequences are available in a variety of plasmids well known in the art. pVH153 was treated with HhaI (which cuts leaving an exposed 3' sticky end just 5' of the trp promoter) blunt-ended with Klenow, and partially digested with TaqI. The 99 bp fragment corresponding to restriction at the TaqI site, 6 nucleotides preceding the ATG start codon of trp leader, was isolated, and then ligated to EcoRI (repair)/ClaI digested, pBR322 to provide pTRP3. pTRP3 was deposited Dec. 18, 1984 and has ATCC Accession No. 39, 946.

E. Expression of Ala$_{104}$ IL-2 in Yeast

The following specific example is used to illustrate additional applications of the process of the invention for the production of alternative active forms of IL-2 in a host other than *E. coli*. In this example, coding sequences having appropriate substitutions to generate any one of several muteins are ligated into a yeast expression vector utilizing the yeast alpha factor promoter, leader, and terminator sequences, and used to produce the desired proteins in yeast.

E.1 Preparation of Reference IL-2 in Yeast

Mature wild-type recombinant IL-2 containing the same amino acid sequence present in the mature IL-2 isolated from human cells was prepared from a cir° derivative of *Saccharomyces cerevisiae* strain C468 (Innis, M. A. et al., *Science* (1985) 228:21–26) transformed with pPM42, an expression vector containing the mature native IL-2 coding sequence fused in frame at its 5' end with the yeast alpha factor signal peptide sequence under the control of the yeast alpha factor promoter. The pPM42 transformed strain was deposited in the American Type Culture Collection on Dec. 13, 1985 and has ATCC Accession No. 53,355.

A seed culture of *S. cerevisiae* transformed with pPM42 was started by thawing a frozen yeast culture (with 10% glycerol) and diluting it 1 to 50 into a selective seed medium containing:

0.01 M succinic acid
5.0 mM H$_3$PO$_4$
3.0 mM H$_2$SO$_4$
5.0 mM Kcl
1.0 mM NaCl
1.0 mM MgCl$_2$·6H$_2$O  0.01 mM MnSO$_4$·H$_2$O  1.0 μM CuSO$_4$·5H$_2$O
5.0 μM ZnSO$_4$·7H$_2$O
5.0 μM CoCl$_2$·6H$_2$O
5.0 μM Na$_2$MoO$_4$·2H$_2$O
0.05 mM H$_3$BO$_3$
0.1 mM CaCl$_2$·2H$_2$O
0.2 g/l histidine The pH was adjusted to 4.25 with NH$_4$OH. After autoclaving, the following sterile additions were made to give final concentrations as shown:

10% glucose
0.5 μg/l pyridoxine HCl
1.0 μg/l thiamine HCl
0.01 μg/l D-biotin
1.0 μg/l calcium pantothenate
0.04 g/l myo-inositol (AKA meso-inositol)
0.04 mM FeSO$_4$ This culture was grown aerobically at 30° C. for 2–3 days until the cell density measured by $A_{680nm}$ reached 10–20.

This culture was then used to inoculate a larger fermenter containing 10 liters of medium. This medium consisted of:

75 mM $NH_4Cl$
5.0 mM $H_3PO_4$
3.0 mM $H_2SO_4$
5.0 mM KCl
1.0 mM NaCl
1.0 mM $MgCl_2 \cdot 6H_2O$
0.01 mM $MnSO_4 \cdot H_2O$
1.0 μM $CuSO_4 \cdot 5H_2O$
5.0 μM $ZnSo_4 \cdot 7H_2O$
5.0 μM $CoCl_2 \cdot 6H_2O$
5.0 μM $Na_2MoO_4 \cdot 2H_2O$
0.05 mM $H_3BO_3$
0.1 mM $CaCl_2 \cdot 2H_2O$
0.5 g/l histidine The pH was adjusted to 5 with 2.5 N NaOH and the mixture was autoclaved. Under sterile conditions (post autoclave), the following additions were made to give final concentrations as shown:

10–15% glucose
0.5 μg/l pyridoxine HCl
1.0 μg/l thiaine HCl
0.01 μg/l D-biotin
1.0 μg/l calcium pantothenate
0.04 g/l myo-inositol (AKA meso-inositol)
0.04 mM $FeSO_4$ Dow Corning Silicon Emulsion B was added to the fermentor on demand to control foaming. The pH of the fermenter was maintained at 4.5 by addition of 4N NaOH, and dissolved oxygen was held at 40% of air saturation by air sparging. The fermenter was agitated at 500 rpm and maintained at 30° C. for 2–3 days until the culture density reached an $A_{680nm}$ of about 20. The cultures were harvested by cell separation and further processing of the culture supernatant.

E.2. Purification of the Reference Protein from Yeast

Cells are separated from the culture supernatant by centrifugation at 4000×g for 15 min. or by cross-flow filtration. The clarified yeast culture supernatant was then concentrated 100–200 fold using a hollow fiber cartridge with a permeability to only molecules of molecular mass of 10,000 daltons or less (e.g. PM10). SDS was added to 2%, and the solution was heated to 37° C. for 20 min. The stabilized IL-2 was then applied to a Sephacryl-200 column (2.6×95 cm) which had been previously equilibrated in 50 mM sodium phosphate pH 7.0 containing 0.2 M NaCl and 0.1% SDS. The protein profile was visualized by absorbance at 280 nm, and the fractions containing low MW proteins were analyzed by SDS-PAGE to locate those most enriched in IL-2.

The IL-2 peak fractions were pooled and concentrated on an Amicon concentrator using a PM10 membrane. Acetonitrile was then added to 10% and the pH was reduced to about 2.5 by the addition of TFA to 0.5% (vol/vol). The IL-2 solution was loaded onto a Bydac $C_4$ column (10 mm×25 cm) and eluted with an acetonitrile gradient of 30–60% in 45 min at a flow rate of 2 ml/min. In some cases (to remove trace contaminants) the IL-2 peak, which eluted later than most of the other contaminating proteins, was diluted 2-fold with 0.1% TFA and rechromatographed on a second Vydac $C_4$ column at a flow rate of 1 ml/min but using otherwise similar conditions to those previously described. The purified IL-2 was then formulated as described above.

E.3. Detection and Analysis of Methionine Sulfoxide-Containing Protein from Yeast When rIL-2 from a culture of *S. cerevisiae* transformed with pPM42 was analyzed by RP-HPLC, two peaks of biologically active IL-2 proteins were resolved. The early eluting peak, Peak A, constituted approximately 15% of the total IL-2 bioactivity recovered. The remainder of the IL-2 eluted somewhat later, in Peak B. Both IL-2 peaks had approximately equivalent biological specific activity in the HT-2 cell proliferation assay described in o.1. The RP-HPLC profile was similar to that of IL-2 produced in *E. coli* in which the early eluting peak, Peak A, was shown to contain a methionine sulfoxide residue at position 104 instead of a methionine found at the same position in the Peak B material.

When an identical purification was carried out on a different aliquot of the same yeast culture supernatant described above which had been previously stored at 4° C. for two weeks, RP-HPLC analysis revealed that about 60% of the IL-2 preparation eluted at the Peak A position. This result suggested that an oxidant was present in the yeast culture supernatant, which, upon storage, was continuing to oxidize the methionine at position 104 in the IL-2 protein.

SDS-PAGE analysis of RP-HPLC Peak A and Peak B material indicated identical molecular weights for the IL-2 from both peaks. Thus, the possibility that proteolysis or differences in glycosylation were the cause of the shift in RP-HPLC retention time seemed unlikely. In addition, experiments performed using specific chemical oxidants such as chloramine T indicate that Peak A arises from Peak B by the oxidation of a specific methionine residue to methionine sulfoxide. The notion that Peak A results from the oxidation of the methionine residue at position 104 in Peak B IL-2 from yeast is confirmed by the absence of Peak A material in muteins containing alanine at position 104 in place of methionine.

Purified Jurkat IL-2 also contains RP-HPLC Peaks A and B. Peak B can be converted to Peak A by in vitro oxidation with chloramine T. By analogy to the yeast and *E. coli* results described above, the Jurkat IL-2 heterogeneity may result from methionine sulfoxide at position 104. Consequently, use of the alanine 104 mutein in mammalian cells might again be expected to reduce IL-2 heterogeneity.

E.4. The Coding Sequence for $Ala_{104}$-Containing IL-2 Muteins in Yeast

An $ala_{104}$ mutein of the wild-type IL-2 of E.1 was prepared by site-specific mutagenesis using an M13 cloned reference protein sequence, prepared substantially as described in U.S. Pat. No. 4,518,584, issued May 21, 1985, and the disclosure of which is incorporated herein by reference. The IL-2 $ala_{104}ala_{125}$ mutein has been obtained by the same procedure.

Briefly, the IL-2 gene from the plasmid pLW32, which was deposited at the American Type Culture Collection on Dec. 13, 1985 and assigned ATCC No. 53,354, was excised as a HindIII-StuI fragment (Wang, A. et al. (1984) *Science* 224:1431–1433; the StuI site is located some 132 bp upstream from the BamII site). A HindIII linker was added to the blunt StuI end of the fragment. This provided a HindIII fragment containing the IL-2 gene for insertion into an M13mp7 vector which had been modified as follows.

An approximately 1.5 kb EcoRI fragment containing the yeast mating factor alpha 1 gene (Singh, A. et al. 91983) *Nucleic Acids Res.* 11:4049–4063) from which the HindIII to SalI fragment (nucleotides 268 to 533) had been deleted to remove the coding sequence for the four copies of the mature alpha-factor, was inserted between the EcoRI sites of M13mp7. Ligation of the HindIII end located 3' of the alpha-factor leader sequence (nucleotide 267) to the repaired SalI end following the fourth copy of the mature alpha-factor coding sequence (nucleotide 534) resulted in the creation of a unique HindIII site in the modified M13mp7 vector (and deletion of the mature alpha-factor coding sequences as just mentioned). The thus modified M13mp7 was designated M13mp7::MFalpha-delta and contained the yeast alpha factor promoter, leader, and terminator sequences with a unique HindII site between the leader and terminator into which a gene of interest could be inserted. M13mp7::MFalpha-delta was deposited at the American Type Culture Collection on Dec. 13, 1985 and assigned ATCC No. 40,210.

The HindIII fragment carrying the IL-2 gene previously described was then inserted into M13mp7::MFalpha-delta at its unique HindIII site. An oligonucleotide primer of the following sequence 5'CTTTGGATAAAAGAGCGCCTACTTCAAG3' was utilized to delete some 16 nucleotides in order to bring the alpha-factor leader peptide sequence and the IL-2 coding sequence into juxtaposition such that the amino acid sequence at the junction was Lys Arg Ala, which can be correctly recognized as a processing site. The resulting construct was designated M13mp7::MFalpha-delta (IL-2), deposited on Dec. 13, 1985 at the ATCC and assigned ATCC No. 40,211.

The EcoRI fragment from M13mp7::MFalpha-delta (IL-2) carrying the alpha-factor promoter, leader, IL-2 gene and alpha-factor terminator was excised and the EcoRI ends were made blunt by repair with DNA polymerase I described in C.4 of the instant application. The plasmid, pJDB219, capable of replicating in both *E. coli* and yeast, has been described (Beggs, J. D. (1978) *Nature* 275:104–109) and contains two TthI sites in a nonessential region of the portion of pJDB219 originally derived from *E. coli* plasmid pMB9 (see FIG. 6). The vector TthI fragment was then replaced by the blunt-ended EcoRI fragment carrying the IL-2 gene. Two orientations of the fragment within the vector are obtained by this method but no difference has been detected between them with regard to IL-2 gene expression. The production of wild type IL-2 was carried out using the construction designated pPM42, in which the IL-2 gene is in the same orientation as the tetracycline resistance (Tet$^R$) gene in pJDB219 (i.e., clockwise in FIG. 6). This plasmid, pPM42, was deposited at the American Type Culture Collection on Dec. 13, 1985 and assigned ATCC No. 53,355.

Ala$_{104}$-containing muteins of IL-2 in yeast were obtained by site-specific mutagenesis using M13mp7::MFalpha-delta (IL-2) as template. To convert the methionine at position 104 to alanine, the oligonucleotide 5'-ACAACATTCGCTTGTGAATATG-03' was synthesized and used substantially as described in D.2. The cysteine at position 125 was converted to alanine using the oligonucleotide primer 5'-GATTACCTTCGCTCAAAGCATC-3'. To produce genes containing more than one modification, successive rounds of mutagenesis each using the appropriate primer were carried out.

E.5. Construction of Expression Vectors Containing Various Ala$_{104}$ IL-2 Muteins Following mutagenesis and selection of the correctly modified coding sequence in M13mp7::MFalpha-delta (IL-2), the IL-2 mutein gene and its control sequence were removed as an EcoRI fragment as described in E.4 for the wild-type IL-2 gene fragment. After DNA polymerase I repair, the blunt-ended fragment containing the IL-2 mutein gene was ligated into pJDB219 between the two TthI sites, thereby replacing the vector fragment. The expression vector that resulted containing the ala$_{104}$ IL-2 mutein was designated pPM43 and was deposited at the American Type Culture Collection on Dec. 13, 1985 and assigned ATCC No. 53,356.

The plasmid DNAs isolated initially from *E. coli* containing the above described construction and pPM42 described in E.4 were transformed into polyethylene glycol (PEG)-treated *S. cerevisiae* strain C468 cir° as detailed below to generate a leu$^+$ phenotype. Cells to be transformed were prepared substantially as described in Klebe, R. J. et al. (1983) *Gene* 25:333–341. Briefly, a single colony was picked into 2 ml YEPD (10 g/l yeast extract; 20 g/l peptone; 2% glucose) and grown overnight at 30° C. The overnight culture was diluted 80-fold into fresh YEPD to provide 10 ml of diluted culture per transformation. Cultures were grown at 30° C. to A$_{600\,nm}$=0.6–0.9, usually about 3–3.5 hrs. Cells were pelleted by a 5 min centrifugation at 4000 rpm (Sorvall JA-20 rotor) at room temperature. Cell pellets were each resuspended in 5 ml SBEG (1M sorbitol, 20 mM bicine pH 8.35, 3% ethylene glycol) and centrifuged again. Cell pellets were each resuspended in 0.2 ml SBEG for 5 min at room temperature. Five to ten μg of transforming DNA was added in no more than 20 μl and the mixture was incubated 10 min at 30° C. The mixture was frozen at −70° C. for at least 10 min. The mixture was thawed in a 37° C. bath and 1.5 ml PEG-bicine (40% PEG-1000; 200 mM bicine pH 8.35) was added. After mixing gently, the transformations were incubated 60 min at 30° C. With gentle mixing, 3 mls NB (150 mM NaCl; 10 mM bicine pH 8.35) was added slowly, and the cells were pelleted by centrifugation in a tabletop centrifuge for 3 min at 2000 rpm. Finally, cells were resuspended in 1 ml NB and plated directly on selective medium (in this case 1.45 g/l Yeast Nitrogen Base (Difco); 0.04 m(NH$_4$)$_2$SO$_4$; 2% glucose; amino acids minus leucine).

To assay the IL-2 bioactivity of yeast transformants, single yeast colonies from selective plates were picked into 3 ml of either selective or non-selective medium and incubated overnight with shaking at 30° C. An aliquot of the culture was removed and filtered through a 0.2 micron filter (Gelman acrodisc) to remove all yeast cells. Supernatants were diluted without further treatment for assay of biological activity as previously described (supra).

E.6. Production and Purification of Ala$_{104}$-Containing IL-2 Muteins from Yeast

*S. cerevisiae* transformed with pPM43 was then grown as described in E.1 above, and the desired oxidation-resistant mutein was purified as described in E.2 above.

E.7. Biochemical and Biological Characterization of the Oxidation-Resistant Mutein from Yeast Yeast cells containing the plasmid pPM43 were grown according to the procedure described in E.1 and $ala_{104}IL-2$ was purified from the culture supernatant as described in E.2. Yeast $ala_{104}IL-2$ was fully active when compared to the reference protein in biological assays such as activation of NK cells, or the IL-2 dependent HT-2 cell proliferation assay. RP-HPLC analysis of the purified oxidation-resistant mutein showed a single symmetrical peak, demonstrating that the Peak A material which was obtained in similarly purified reference IL-2 had been eliminated. The RP-HPLC retention time of the mutein different slightly from that of the reference protein, as had been observed for other IL-2 point mutations, including des-$ala_1ala_{104}ser_{125}IL-2$ in *E. coli* (Kunitani, et al., Fifth Int'l symposium on HPLC of Proteins, Peptides and Polynucleotides, Toronto, Canada, Nov. 4–6, 1985).

Chloramine T treatment of this preparation conducted exactly as set forth above for the reference IL-2 shows no change in the RP-HPLC pattern, indicating that this mutein lacks the methionine residue preferentially susceptible to oxidation by chloramine T.

F. Preparation of Oxidation-Resistant Muteins of IFN-β

Recombinant $ser_{17}IFN-\beta$ containing a methionine residue at position 62 may be modified to produce muteins such as $ser_{17}ala_{62}IFN-\beta$, or $ala_{62}IFN-\beta$. The construction of the potentially oxidation-resistant mutein, $ser_{17}ala_{62}IFN-\beta$, is described.

Preparation of Coding Sequence

A clone, designated as M13-SY2501 and containing the coding sequence for $ser_{17}IFN-\beta$, was prepared as described in Mark, D. F. et al. (1984) *Proc. Natl. Acad. Sci. USA* 81:5662–5666. This clone was used as a template for oligonucleotide-directed mutagenesis to convert the methionine at position 62 to an alanine residue. 40 pmoles of the oligonucleotide 5'-CCATCTAT-GAGGCGCTGCAGAACATC-3' was kinased under standard conditions for use as primer and probe. Ten pmoles of the kinased primer was hybridized to 2.6 μg of single-stranded (SS) M13-SY2501 in 15 μl of a mixture containing 100 mM NaCl, 20 mM Tris-HCl, pH 7.9, 20 mM $MgCl_2$, and 20 mM β-mercaptoethanol by heating at 67° C. for five minutes and 42° C. for 25 minutes. The annealed mixture was chilled on ice and adjusted to a final volume of 25 μl in a reaction mixture containing 0.5 mM of each dNTP, 17 mM Tris-HCl, pH 7.9, 17 mM $MgCl_2$, 83 mM NaCl, 17 mM β-mercaptoethanol, 5 units of DNA polymerase I, Lkenow fragment, 0.5 mM ATP, and 2 units of $T_4$ DNA ligase, incubated at 37° C. for 30 minutes. The reactions were terminated by heating to 70° C. The reaction mixtures were used to transform competent *E. coli* K12 DG 98 cells, which were plated onto agar plates, and incubated overnight to obtain phage plaques. DG 98 cells are described more fully in copending EP Publication No. 137,280 published Apr. 17, 1985, and were deposited with the American Type Culture Collection, Rockville, Md. on Jul. 13, 1984 under ATCC No. 39,768. The plaques were probed using kinased primer using standard prehybridization and hybridization conditions at high stringency (60° C. for two hours). A plaque which hybridized to primer was selected. This plaque was designated M13-DM101 and contains the coding sequence for $ser_{17}ala_{62}IFN-\beta$.

Construction of Expression Clone

To construct the host vector containing the trp control sequences behind a HindII site, the trp promoter/operator/ribosome binding site sequence, lacking the attenuator region, was derived from pVH153, obtained from C. Yanofsky, Stanford University, Stanford, Calif. Trp sequences are available in a variety of plasmids well known in the art. pVH153 was treated with HhaI (which cuts, leaving an exposed 3' sticky end just 5' of the trp promoter), blunt-ended with Klenow, and partially digested with TaqI. The 99 bp fragment corresponding to restriction at the TagI site, six nucleotides preceding the ATG start codon of trp leader, was isolated, and then ligated to EcoRI (repair)/ClaI digested, pBR322 to provide pTRP3. pTRP3 was deposited on Dec. 18, 1984 and has ATCC Accession No. 39,946.

RF-DNA from M13-DM101 was digested with HindIII and XhoII, and the fragment containing the mutagenized IFN-β coding sequence was purified from a 1% agarose gel and inserted into the HindIII and BamHI sites of plasmid pTRP3, described above, containing the trp promoter. The ligation mixture was transformed into competent *E. coli* K12 strain MM294, generating an ampicillin-resistant phenotype. The resulting clone, designated pAW207, containing the coding sequence for $ser_{17}ala_{62}IFN-\beta$ was confirmed by restriction analysis and dideoxy sequencing. This clone was deposited with the American Type Culture Collection (ATCC), 12301 Parklawn Drive, Rockville, Md. under ATCC No. 67,138 on Jun. 19, 1986.

Production and Purification of $Ser_{17}Ala_{62}IFN-\beta$

For growth of *E. coli* transformed with this expression clone, the following basal medium was used:

| | |
|---|---|
| $NH_4Cl$ | 10 mM |
| $KH_2PO_4$ | 21.9 mM |
| $Na_2HPO_4$ | 28.1 mM |
| $K_2SO_4$ | 9 mM |
| $MgSO_4$ | 2 mM |
| $MnSO_4$ | 3 μM |
| $ZnSO_4$ | 3 μM |
| $CuSO_4$ | 0.1 μM |
| $FeSO_4$ | 10 μM |
| Glucose | 2 g/l |
| Ampicillin | 50 mg/l |

An overnight culture was grown at 37° C. in the above medium supplemented with 50 mg/l L-tryptophan. The cells were washed once in basal medium and resuspended in basal medium supplemented with casamino acids (20 g/l) and β-indole acrylic acid (10 mg/l), to an optical density of 0.2 (680 nm). The culture was shaken at 37° C. for four hours, and the cells were harvested by centrifugation. Approximately 300 mg dry weight cells was derived from a 750 ml culture by centrifugation.

The cells were then resuspended in 2% SDS in phosphate buffered saline (PBS) (consisting of 0.15 M NaCl, 0.0175 m $NaPO_4$, and 0.01475 M NaOH) and disrupted by sonication. Solid dithiothreitol (DTT) was then added to a final concentration of 10 mM and the homogenate was treated to 50±5° C. for 10 minutes. The resulting solubilized cell disruptate was extracted with 2-butanol and 2 mM dithiothreitol (DTT) at 1:1 2- butanol/DTT:suspension volume ratio in a static mixer. The mixture was then centrifuged and the 2-butanol-rich phase was collected.

The 2-butanol-rich phase was mixed with 2.5 volumes of 0.1% w/v SDS in PBS. The pH of the mixture was adjusted to 6.2±0.1 with glacial acetic acid and this mixture was centrifuged. The resulting paste was collected and resuspended in a mixture of 50 mM NaPO$_4$, 5 mM EDTA and 5% SDS with pH adjustment to 8.5±0.1 using 1 N NaOH. Solid DTT was added to a final concentration of 10 mM and the suspension was heated to 50±5° C. for 10 minutes. The suspension was then cooled to about 25° C., the pH was adjusted to 5.5±0.1 with glacial acetic acid, and the solution was filtered.

The solution was then applied to a Sephadex G-25 desalting column which was equilibrated with 50 mM sodium phosphate, 0.1% SDS, pH 7.0. The peak, A$_{280}$ absorbing fraction was pooled.

The protein was oxidized to generate disulfide bonds. The reaction mixture contained approximately 0.25 mg/ml of the interferon. Oxidation was initiated by adding CuCl$_2$ to a final concentration of 1 mM at 25° C.

The oxidized product was applied to a 1.3 cm Vydac ™ C$_4$ preparative RP-HPLC column in a water-:acetonitrile gradient in 0.1% v/v trifluoroacetic acid to separate the oxidized interferon from the E. coli contaminant proteins. The IFN peak was pooled and the pool was subjected to an analytical RP-HPLC in the same gradient.

Activity of Mutein

When tested for antiviral activity using the yield reduction assay described by Steward and Lockhart, supra, the oxidized mutein was found to have approximately 13% of the specific activity of the ser$_{17}$IFN-$\beta$ mutein described in U.S. Pat. No. 4,588,585 issued May 13, 1986.

Homogeneity of the Mutein

When the mutein was subjected to the analytical RP-HPLC, a single symmetrical peak was obtained, showing that the Peak A impurity material which was observed in the RP-HPLC of similarly purified ser$_{17}$IFN-$\beta$, ser$_{17}$ala$_{36}$IFN-$\beta$, and ser$_{17}$ala$_{17}$IFN-$\beta$ has been eliminated. (The correlation of Peak A with an oxidized methionine in ser$_{17}$IFN-$\beta$ was confirmed by oxidizing the ser$_{17}$IFN-$\beta$ sample with hydrogen peroxide and comparing the pre-oxidation and post-oxidation RP-HPLC profiles.)

The mutein was then oxidized with 0.5% hydrogen peroxide at pH 5.0 and then analyzed by analytical RP-HPLC. No change in the RP-HPLC pattern was obtained for the oxidized mutein, indicating that this mutein lacks the methionine residue preferentially susceptible to oxidation to Peak A by hydrogen peroxide. The main peak for the oxidized ser$_{17}$ala$_{62}$IFN-$\beta$ mutein was, however, shifted in the RP-HPLC compared to the main peak for the unoxidized form, indicating that perhaps other unsubstituted methionines in the mutein or other amino acids were being oxidized to some extent, but not to a species corresponding to Peak A.

At least any one of the first five amino acids may be deleted, in any combination, or substituted by another amino acid, at the N-terminus of the oxidation-resistant IL-2 mutein with retention of biological activity. A similar possibility may exist with regard to other oxidation-resistant muteins such as IFN-$\beta$. In addition, a substitution of a conservative amino acid such as alanine or serine at position 125 of the IL-2 mutein or at position 17 of the IFN-$\beta$ mutein may be made to confer additional stability on the mutein, by replacing cysteine residues which are not essential to the biological activity of the mutein. Any permutation of any of these changes alone or in combination with one or more other of these changes may be made to the oxidation-resistant muteins herein. For example, the following muteins are within the scope of this invention: ala$_{62}$IFN-$\beta$, ser$_{17}$ala$_{62}$IFN-$\beta$, val$_{62}$IFN-$\beta$, ser$_{17}$val$_{62}$IFN-$\beta$, leu$_{62}$IFN-$\beta$, ser$_{17}$leu$_{62}$IFN-$\beta$, ala$_{104}$ser$_{125}$IL-2, ala$_{104}$IL-2, ala$_{104}$ala$_{125}$IL-2, val$_{104}$ser$_{125}$IL-2, val$_{104}$IL-2, val$_{104}$ala$_{125}$IL-2, des-ala$_1$ala$_{104}$ser$_{125}$IL-2, des-ala$_1$ala$_{104}$IL-2, des-ala$_1$ala$_{104}$ala$_{125}$IL-2, des-ala$_1$val$_{104}$ser$_{125}$IL-2, des-ala$_1$val$_{104}$IL-2, des-ala$_1$val$_{104}$ala$_{125}$IL-2, des-ala$_1$des-pro$_2$ala$_{104}$ser$_{125}$IL-2, des-ala$_1$des-pro$_2$ala$_{104}$IL-2, des-ala$_1$des-pro$_2$ala$_{104}$ala$_{125}$IL-2, des-ala$_1$des-pro$_2$val$_{104}$ser$_{125}$IL-2, des-ala$_1$des-pro$_2$val$_{104}$IL-2, des-ala$_1$des-pro$_2$val$_{104}$ala$_{125}$IL-2, des-ala$_1$des-pro$_2$des-thr$_3$ala$_{104}$ser$_{125}$IL-2, des-ala$_1$des-pro$_2$des-thr$_3$ala$_{104}$IL-2, des-ala$_1$des-pro$_2$des-thr$_3$ala$_{104}$ala$_{125}$IL-2, des-ala$_1$des-pro$_2$des-thr$_3$val$_{104}$ser$_{125}$IL-2, des-ala$_1$des-pro$_2$des-thr$_3$val$_{104}$IL-2, des-ala$_1$des-pro$_2$des-thr$_3$val$_{104}$ala$_{125}$IL-2, des-ala$_1$des-pro$_2$des-thr$_3$des-ser$_4$ala$_{104}$ser$_{125}$IL-2, des-ala$_1$des-pro$_2$des-thr$_3$des-ser$_4$ala$_{104}$IL-2, des-ala$_1$des-pro$_2$des-thr$_3$des-ser$_4$ala$_{104}$ala$_{125}$IL-2, des-ala$_1$des-pro$_2$des-thr$_3$des-ser$_4$val$_{104}$ser$_{125}$IL-2, des-ala$_1$des-pro$_2$des-thr$_3$des-ser$_4$val$_{104}$IL-2, des-ala$_1$des-pro$_2$des-thr$_3$des-ser$_4$val$_{104}$ala$_{125}$IL-2, des-ala$_1$des-pro$_2$des-thr$_3$des-ser$_4$ser$_5$ala$_{104}$ser$_{125}$IL-2, des-ala$_1$des-pro$_2$des-thr$_3$des-ser$_4$des-ser$_5$ala$_{104}$IL-2, des-ala$_1$des-pro$_2$des-thr$_3$des-ser$_4$des-ser$_5$ala$_{104}$ala$_{125}$IL-2, des-ala$_1$des-pro$_2$des-thr$_3$des-ser$_4$des-ser$_5$val$_{104}$ser$_{125}$IL-2, des-ala$_1$des-pro$_2$des-thr$_3$des-ser$_4$des-ser$_5$val$_{104}$IL-2, des-ala$_1$des-pro$_2$des-thr$_3$des-ser$_4$des-ser$_5$val$_{104}$ala$_{125}$IL-2, des-ala$_1$des-pro$_2$des-thr$_3$des-ser$_4$des-ser$_5$des-ser$_6$ala$_{104}$ala$_{125}$IL-2, des-ala$_1$des-pro$_2$des-thr$_3$des-ser$_4$des-ser$_5$des-ser$_6$ala$_{104}$IL-2, des-ala$_1$des-pro$_2$des-thr$_3$des-ser$_4$des-ser$_5$des-ser$_6$ala$_{104}$ser$_{125}$IL-2, des-ala$_1$des-pro$_2$des-thr$_3$des-ser$_4$des-ser$_5$des-ser$_6$ala$_{104}$ser$_{125}$IL-2, des-ala$_1$des-pro$_2$des-thr$_3$des-ser$_4$des-ser$_5$des-ser$_6$ala$_{104}$IL-2, and des-ala$_1$des-pro$_2$des-thr$_3$des-ser$_4$des-ser$_5$des-ser$_6$ala$_{104}$ser$_{125}$IL-2.

Applicants have deposited the following cultures with the American Type Culture Collection, Rockville, Md., U.S.A. (ATCC):

| Strain | ATCC Deposit No. | Deposit Date |
| --- | --- | --- |
| pLW55 | 39,516 | 11/18/83 |
| pTRP3 | 39,946 | 12/18/84 |
| pSY3001 in E. coli K12 strain MM294 | 39,949 | 12/19/84 |
| M13mp7::MF alpha-delta | 40,210 | 12/13/85 |
| M13mp7::MF alpha-delta (IL-2) | 40,211 | 12/13/85 |
| pLW32 | 53,354 | 12/13/85 |
| pPM42 | 53,355 | 12/13/85 |
| pPM43 | 53,356 | 12/13/85 |
| S. cerevisiae C468 cir° | 20,787 | 12/13/85 |
| pAW207 | 67,138 | 6/19/86 |

These deposits were made under the provisions of the Budapest Treaty on the International Recognition of the Deposit of Microorganisms for the Purposes of Patent Procedure and the Regulations thereunder (Budapest Treaty). This assures maintenance of a viable culture for 30 years from data of deposit. The organisms will be made available by ATCC under the terms of the Budapest Treaty, and subject to an agreement between applicants and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the cultures on deposit should die or be lost or destroyed when cultivated under suitable conditions, they will be promptly replaced on notification with a viable specimen of the same culture. Availability of the deposited strains is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the constructs deposited, since the deposited embodiment is intended as a single illustration of one aspect of the invention and any constructs which are functionally equivalent are within the scope of this invention. The deposit of materials herein does not constitute an admission that the written description herein contained is inadequate to enable the practice of any aspect of the invention, including the best mode thereof, nor are they to be construed as limiting the scope of the claims to the specific illustrations which they represent. Indeed, various modifications of the invention in addition to those shown and described herein will become apparent to those skilled in the art from the foregoing description and fall within the scope of the appended claims.

What is claimed is:

1. An oxidation-resistant IL-2 mutein having therapeutically useful biological activity, wherein each methionine residue of a reference protein susceptible to chloramine T or peroxide oxidation is replaced by a conservative amino acid, and wherein additional, non-susceptible methionine residues are not so substituted.

2. The oxidation-resistant mutein of claim 1 wherein the conservative amino acid is selected from the group consisting of glycine, alanine, serine, threonine, valine, isoleucine, leucine, asparagine, glutamine, glutamate, tyrosine, and phenylalanine.

3. The oxidation-resistant mutein of claim 2 wherein the reference protein is human.

4. The oxidation-resistant mutein of claim 2 wherein the conservative amino acid is selected from the group consisting of alanine, serine, leucine, isoleucine, glutamate and valine.

5. The oxidation-resistant mutein of claim 4 selected from the group consisting ala$_{104}$ser$_{125}$IL-2, ala$_{104}$ala$_{125}$IL-2, val$_{104}$ser$_{125}$IL-2, val$_{104}$IL-2, val$_{104}$ala$_{125}$IL-2, des-ala$_1$ala$_{104}$ser$_{125}$IL-2, des-ala$_1$ala$_{104}$ IL-2, des-ala$_1$ala$_{104}$ala$_{125}$IL-2, des-ala$_1$val$_{104}$ser$_{125}$IL-2, des-ala$_1$val$_{104}$IL-2, des-ala$_1$val$_{104}$ala$_{125}$IL-2, des-ala$_1$des-pro$_2$ala$_{104}$ser$_{125}$IL-2, des-ala$_1$des-pro$_2$ala$_{104}$IL-2, des-ala$_1$des-pro$_2$ala$_{104}$ala$_{125}$IL-2, des-ala$_1$des-pro$_2$val$_{104}$ser$_{125}$IL-2, des-ala$_1$des-pro$_2$val$_{104}$IL-2, des-ala$_1$des-pro$_2$val$_{104}$ala$_{125}$IL-2, des-ala$_1$des-pro$_2$des-thr$_3$ala$_{104}$ser$_{125}$IL-2, des-ala$_1$des-pro$_2$des-thr$_3$ala$_{104}$IL-2, des-ala$_1$des-pro$_2$des-thr$_3$ala$_{104}$ala$_{125}$IL-2, des-ala$_1$des-pro$_2$des-thr$_3$val$_{104}$ser$_{125}$IL-2, des-ala$_1$des-pro$_2$des-thr$_3$val$_{104}$IL-2, des-ala$_1$des-pro$_2$des-thr$_3$val$_{104}$ala$_{125}$IL-2, des-ala$_1$des-pro$_2$des-thr$_3$des-ser$_4$ala$_{104}$ser$_{125}$IL-2, des-ala$_1$des-pro$_2$des-thr$_3$des-ser$_4$ala$_{104}$IL-2, des-ala$_1$des-pro$_2$des-thr$_3$des-ser$_4$ ala$_{104}$ala$_{125}$IL-2, des-ala$_1$des-pro$_2$des-thr$_3$des-ser$_4$val$_{104}$ser$_{125}$IL-2, des-ala$_1$des-pro$_2$des-thr$_3$des-ser$_4$val$_{104}$IL-2, des-ala$_1$des-pro$_2$des-thr$_3$des-ser$_4$val$_{104}$ala$_{125}$IL-2, des-ala$_1$des-pro$_2$des-thr$_3$des-ser$_4$des-ser$_5$ala$_{104}$ser$_{125}$IL-2, des-ala$_1$des-pro$_2$des-thr$_3$des-ser$_4$des-ser$_5$ala$_{104}$IL-2, des-ala$_1$des-pro$_2$des-thr$_3$des-ser$_4$des-ser$_5$ala$_{104}$ala$_{125}$IL-2, des-ala$_1$des-pro$_2$des-thr$_3$des-ser$_4$des-ser$_5$val$_{104}$ser$_{125}$IL-2, des-ala$_1$des-pro$_2$des-thr$_3$des-ser$_4$des-ser$_5$val$_{104}$IL-2, des-ala$_1$des-pro$_2$des-thr$_3$des-ser$_4$des-ser$_5$val$_{104}$ala$_{125}$IL-2, des-ala$_1$des-pro$_2$des-thr$_3$des-ser$_4$des-ser$_5$des-ser$_6$ala$_{104}$ala$_{125}$IL-2, des-ala$_1$des-pro$_2$des-thr$_3$des-ser$_4$des-ser$_5$des-ser$_6$ala$_{104}$IL-2, des-ala$_1$des-pro$_2$des-thr$_3$des-ser$_4$des-ser$_5$des-ser$_6$ala$_{104}$ser$_{125}$IL-2, des-ala$_1$des-pro$_2$des-thr$_3$des-ser$_4$des-ser$_5$des-ser$_6$ala$_{104}$ser$_{125}$IL-2, des-ala$_1$des-pro$_2$des-thr$_3$des-ser$_4$des-ser$_5$des-ser$_6$ala$_{104}$IL-2, and des-ala$_1$des-pro$_2$des-thr$_3$des-ser$_4$des-ser$_5$des-ser$_6$ala$_{104}$ser$_{125}$IL-2.

6. The oxidation-resistant mutein of claim 5 selected from the group consisting of ala$_{104}$ser$_{125}$IL-2, ala$_{104}$IL-2, ala$_{104}$ala$_{125}$IL-2, des-ala$_1$ala$_{104}$IL-2, des-ala$_1$ala$_{104}$ser$_{125}$IL-2, or des-ala$_1$ala$_{104}$ala$_{125}$IL-2.

7. A human IL-2 oxidation-resistant mutein having a conservative amino acid substitution at position 104, wherein the reference IL-2 protein contains a methionine at position 104, and wherein said mutein exhibits the biological activity of human IL-2.

8. The mutein of claim 7 wherein the conservative amino acid is selected from the group consisting of glycine, alanine, serine, threonine, valine, isoleucine, leucine, asparagine, glutamine, glutamate, tyrosine, and phenylalanine.

9. The mutein of claim 8 wherein the amino acid is selected from the group consisting of alanine, serine, leucine, glutamate, and valine.

10. The mutein of claim 9 wherein the protein is unglycosylated and the amino acid is serine or alanine.

11. A therapeutic formulation comprising an effective amount of the mutein of claim 7 and an inert, non-allergenic, pharmaceutically compatible carrier.

12. The formulation of claim 11 wherein the mutein is an ala$_{104}$IL-2 mutein, and the carrier is selected from the group consisting of distilled water, physiological saline, Ringer's solution, and Hank's solution.

13. The formulation of claim 12, further comprising non-toxic stabilizers and solubilizers.

* * * * *

UNITED STATES PATENT AND TRADEMARK OFFICE
CERTIFICATE OF CORRECTION

PATENT NO. : 5,116,943                      Page 1 of 2

DATED     : May 26, 1992

INVENTOR(S) : K. Koths et al

It is certified that error appears in the above-identified patent and that said Letters Patent is hereby corrected as shown below:

Title page, item [54], and col. 1, line 2, "PROTEIN" should read
--PROTEINS--.

Title page, item [75], "Danutee Nitecti" should read
Danute Nitecki--.

On title page, at item [56], under "OTHER PUBLICATIONS" please delete the "a" in "Zoller et al.".

At column 3, lines 50-51, after "native", please delete "be-tainterferon" and replace therefor --beta-interferon--.

At column 6, line 34, after "resolve", please delete "preference" and replace therefor --reference--.

UNITED STATES PATENT AND TRADEMARK OFFICE
CERTIFICATE OF CORRECTION

PATENT NO. : 5,116,943

DATED : May 26, 1992

INVENTOR(S) : K. Koths et al.

It is certified that error appears in the above-identified patent and that said Letters Patent is hereby corrected as shown below:

At column 7, line 10, after "others", please delete "area" and replace therefor --are--.

At column 7, line 32, after "consist of", please delete "phase" and replace therefor --phage--.

At column 9, line 1, after "instead of", please delete "cysteiene" and replace therefor --cysteine--.

At column 15, line 43, after "Intermolecular", please delete "'stick end'", and replace therefor --"sticky end"--.

At column 17, line 4, after "mutein", please delete "des-ala$_2$ser$_{125}$", and replace therefor --des-ala$_1$ser$_{125}$--.

At column 29, line 45, after "and", please delete "ser$_{17}$ala$_{17}$IFN-$\beta$", and replace therefor --ser$_{17}$ala$_{117}$IFN-$\beta$--.

At column 32, line 34, after the second reference to "ala$_{104}$", please delete "IL$_2$", and replace therefor --IL-2--.

Signed and Sealed this

Third Day of August, 1993

Attest:

MICHAEL K. KIRK

*Attesting Officer*  Acting Commissioner of Patents and Trademarks

UNITED STATES PATENT AND TRADEMARK OFFICE
CERTIFICATE OF CORRECTION

PATENT NO. : 5,116,943
DATED : May 26, 1992
INVENTOR(S) : Kirston E. Koths, Robert F. Halenbeck, David F. Mark and Danute Nitecti It is certified that error appears in the above-indentified patent and that said Letters Patent is hereby corrected as shown below:

On drawing sheet on sheet 2, FIG. 3D after "$ala_1$", and before "$ser_{125}$", please insert --$ala_{104}$--.

On sheet 5 of drawing, FIG. 6, "2560" and "3860" should read "~2560" and "~3860".

At column 1, line 17, after "i.e.", please delete "oxidation-receptive" and substitute --oxidation-resistant-- therefor.

Signed and Sealed this

Sixth Day of September, 1994

Attest:

BRUCE LEHMAN

Attesting Officer     Commissioner of Patents and Trademarks